(12) United States Patent
Ijdo et al.

(10) Patent No.: US 11,318,082 B2
(45) Date of Patent: *May 3, 2022

(54) CROSSLINKABLE COATING COMPOSITIONS FORMULATED WITH DORMANT CARBAMATE INITIATOR

(71) Applicant: ELEMENTIS SPECIALTIES, INC., East Windsor, NJ (US)

(72) Inventors: Wouter Ijdo, Yardley, PA (US); Yanhui Chen, Princeton, NJ (US); Prashant Deshmukh, Plainsboro, NJ (US); Rajni Gupta, Princeton, NJ (US); James A. Heck, Robbinsville, NJ (US); Wayne Hoyte, Parlin, NJ (US); Maurice Gray, Saint Albans, NY (US)

(73) Assignee: ELEMENTS SPECIALTIES, INC., East Windsor, NJ (US)

( * ) Notice: Subject to any disclaimer, the term of this patent is extended or adjusted under 35 U.S.C. 154(b) by 20 days.

This patent is subject to a terminal disclaimer.

(21) Appl. No.: 16/999,505

(22) Filed: Aug. 21, 2020

(65) Prior Publication Data

US 2021/0007963 A1 Jan. 14, 2021

Related U.S. Application Data

(63) Continuation of application No. 16/822,958, filed on Mar. 18, 2020, now Pat. No. 10,799,443, which is a (Continued)

(51) Int. Cl.
| | |
|---|---|
| *A61K 8/85* | (2006.01) |
| *A61K 8/81* | (2006.01) |
| *A61K 8/40* | (2006.01) |
| *A61K 8/04* | (2006.01) |
| *A61Q 3/02* | (2006.01) |

(Continued)

(52) U.S. Cl.
CPC ............... *A61K 8/85* (2013.01); *A61K 8/042* (2013.01); *A61K 8/40* (2013.01); *A61K 8/8152* (2013.01); *A61Q 3/02* (2013.01); *C07C 209/68* (2013.01); *C07C 211/63* (2013.01); *C07C 269/06* (2013.01); *C07C 271/02* (2013.01); *C08G 63/672* (2013.01); *C09D 167/025* (2013.01); *A61K 2800/43* (2013.01); *A61K 2800/48* (2013.01); *A61K 2800/592* (2013.01); *A61K 2800/594* (2013.01); *A61K 2800/81* (2013.01); *A61K 2800/95* (2013.01)

(58) Field of Classification Search
CPC . A61K 8/85; A61K 8/042; A61K 8/40; A61K 8/8152; A61K 2800/43; A61K 2800/48; A61K 2800/592; A61K 2800/594; A61K 2800/81; A61K 2800/95; A61K 8/44; C09D 7/63; C09D 167/06; C09D 167/08; C09D 171/00; C09D 175/14; A61Q 3/02; C07C 209/68; C07C 211/63; C07C 269/06; C07C 27/012; C08G 63/672

See application file for complete search history.

(56) References Cited

U.S. PATENT DOCUMENTS

| 5,801,213 A | 9/1998 | Schwalm et al. |
|---|---|---|
| 8,003,169 B2 | 8/2011 | Misev et al. |
| (Continued) | | |

FOREIGN PATENT DOCUMENTS

| CN | 102834437 B | 9/2015 |
|---|---|---|
| EP | 0284561 A | 9/1998 |
| (Continued) | | |

OTHER PUBLICATIONS

Search Report dated Oct. 20, 2021 in corresponding Brazilian Patent Application No. BR112018075947-3 (English version included).
Examination Report dated Nov. 10, 2021 in corresponding Argentine Patent Application No. 20170101784 (English version included).
First Office Action for corresponding Chinese Patent Application No. 201780038962.8 dated Aug. 7, 2020, 20 pages.
Office Action for corresponding Chinese Patent Application No. 201780038962.8 dated Apr. 23, 2021, 6 pages.
Extended European Search Report for corresponding Application No. EP 20 21 4006 dated Apr. 1, 2021, 8 pages.
Ulf P. Kreher et al.: "Direct Preparation of Monoarylidene Derivatives of Aldehydes and Enolizable Ketones with DIMCARB", Organic Letters, vol. 15, No. 17, Aug. 1, 2003, pp. 3107-3110.

(Continued)

*Primary Examiner* — Quanglong N Truong
(74) *Attorney, Agent, or Firm* — Morgan, Lewis & Bockius LLP

(57) ABSTRACT

A crosslinkable coating composition comprising: ingredient A that has at least two protons that can be activated to form a Michael carbanion donor; ingredient B that functions as a Michael acceptor having at least two ethylenically unsaturated functionalities each activated by an electron-withdrawing group; and a dormant carbamate initiator of Formula (1)

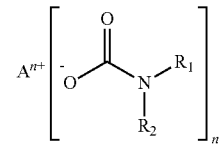

wherein $R_1$ and $R_2$ can be independently selected from hydrogen, a linear or branched substituted or unsubstituted alkyl group having 1 to 22 carbon atoms; 1 to 8 carbon atoms; and $A^{n+}$ is a cationic species or polymer and n is an integer equal or greater than 1 with the proviso that $A^{n+}$ is not an acidic hydrogen; and optionally further comprising ammonium carbamate $(H_2NR_1R_2{}^{+-}OC{=}ONR_1R_2)$. The crosslinkable coating composition can be used for a variety of coating applications including nail coating compositions.

17 Claims, No Drawings

Related U.S. Application Data continuation of application No. 15/621,504, filed on Jun. 13, 2017, now Pat. No. 10,624,833.

(60) Provisional application No. 62/356,918, filed on Jun. 30, 2016.

(51) Int. Cl.
| | |
|---|---|
| *C07C 209/68* | (2006.01) |
| *C07C 211/63* | (2006.01) |
| *C07C 269/06* | (2006.01) |
| *C07C 271/02* | (2006.01) |
| *C08G 63/672* | (2006.01) |
| *C09D 167/02* | (2006.01) |

(56) References Cited

U.S. PATENT DOCUMENTS

| | | |
|---|---|---|
| 8,962,725 B2 | 2/2015 | Brinkhuis et al. |
| 9,181,452 B2 | 11/2015 | Brinkhuis et al. |
| 9,181,453 B2 | 11/2015 | Brinkhuis et al. |
| 9,260,626 B2 | 2/2016 | Brinkhuis et al. |
| 9,284,423 B2 | 3/2016 | Brinkhuis et al. |
| 9,328,187 B2 | 5/2016 | Mestach et al. |
| 9,534,081 B2 | 1/2017 | Brinkhuis et al. |
| 2005/0143575 A1 | 6/2005 | Bernard |
| 2009/0120800 A1 | 5/2009 | Chung et al. |
| 2009/0269595 A1 | 10/2009 | Chung et al. |
| 2011/0201742 A1 | 8/2011 | Parent et al. |
| 2013/0041091 A1 | 2/2013 | Brinkhuis et al. |
| 2013/0072641 A1 | 3/2013 | Mestach et al. |
| 2014/0220252 A1 | 8/2014 | Brinkhuis et al. |
| 2014/0221542 A1 | 8/2014 | Brinkhuis et al. |
| 2015/0376472 A1 | 12/2015 | Bzowej et al. |
| 2016/0060389 A1 | 3/2016 | Brinkhuis et al. |
| 2016/0060482 A1 | 3/2016 | Brinkhuis et al. |
| 2016/0115344 A1 | 4/2016 | Brinkhuis et al. |
| 2016/0168320 A1 | 6/2016 | Brinkhuis et al. |
| 2016/0311957 A1 | 10/2016 | Mestach et al. |
| 2016/0333199 A1 | 11/2016 | Akkerman et al. |

FOREIGN PATENT DOCUMENTS

| | | |
|---|---|---|
| EP | 2374836 A1 | 10/2011 |
| GB | 2405149 A | 2/2005 |
| WO | 1998032756 A1 | 7/1998 |
| WO | WO 98/32756 A1 | 7/1998 |
| WO | WO 99/14278 A1 | 3/1999 |
| WO | WO 99/14279 A1 | 3/1999 |
| WO | WO 2008/07022 A1 | 6/2008 |
| WO | 2011121085 A1 | 10/2011 |
| WO | 2011124663 A1 | 10/2011 |
| WO | 2011124664 A1 | 10/2011 |
| WO | 2011124665 A1 | 10/2011 |
| WO | 2013050574 A1 | 4/2013 |
| WO | 2013050623 A1 | 4/2013 |
| WO | 2016166334 A1 | 10/2016 |
| WO | 2016166361 A1 | 10/2016 |
| WO | 2016166365 A1 | 10/2016 |
| WO | 2016166369 A1 | 10/2016 |
| WO | 2016166371 A1 | 10/2016 |
| WO | 2016166381 A1 | 10/2016 |

OTHER PUBLICATIONS

Office Action for corresponding Japanese Patent Application No. JP 2018-564892 dated Mar. 30, 2021, 6 pages.
"Electrolysis of Ammonium Carbamate: A Voltammetric and X-ray Photoelectron Spectroscopic Investigation into the Modification of Carbon Electrodes", Int. J Electrochem. Sci., 2 (2007) 809-819.
Examination Report for corresponding Indian Application No. 201817046788 dated Jan. 2, 2021, 6 pages.
Office Action for corresponding Taiwan Application No. 106121133 dated Feb. 20, 2021, 9 pages.
Ulf P. Kreher, "Direct Preparation of Monoarylidene Derivatives of Aldehydes and Enolizable Ketones with DIMCARB", Organic Letters 2003 vol. 5, No. 17, 3107-3110.
Extended Search Report of European Application No. EP 17820888 dated Mar. 16, 2020.
PCT/US2017/037176 Preliminary Report on Patentability dated Jan. 10, 2019; 8 pages.
Wildgoose et al., "Electrolosis of Ammonium Carbamate: A Voltammetric and X-Ray Photoelectron Spevtroscopic Investigation into the Modification of Carbon Electrodes", Int. J. Electrochem, Sci., vol. 2, pp. 809-819 (2007).
International Search Report issued for corresponding application, PCT/US17/37176 dated Aug. 29, 2017.
Written Opinion issued for corresponding application, PCT/US17/37176 dated Aug. 29, 2017.
John, "Novel Switchable Systems and Application", A Thesis Presented to the Academic Faculty, Georgia Institute of Technology, (2007).
Khunsupat, "Poly(Allylamine) and Derivatives for CO2 Capture from Flue Gas or Ultra-Dilute Gas Streams Such as Ambient Air", A Thesis Presented to the Academic Faculty, Georgia Institute of Technology (2011).
Notice of Preliminary Rejection dated Dec. 13, 2021 in corresponding Korean Patent Application No. 10-2019-7001730 (English version included).

CROSSLINKABLE COATING COMPOSITIONS FORMULATED WITH DORMANT CARBAMATE INITIATOR

CROSS-REFERENCE TO RELATED APPLICATIONS

The application is a continuation of prior U.S. application Ser. No. 16/822,958, filed Jun. 9, 2020, which is a continuation of U.S. application Ser. No. 15/621,504, filed Jun. 13, 2017, now U.S. Pat. No. 10,624,833, which claims priority benefit from U.S. Provisional Patent Application 62/356,918 filed Jun. 30, 2016, each of which is incorporated by reference herein in its entirety.

FIELD OF THE INVENTION

The invention provides for a crosslinkable composition using a dormant carbamate initiator for use in various coating compositions such as nail coating compositions.

BACKGROUND OF THE INVENTION

The coatings industry continues to develop new chemistries as performance requirements for decorative and functional coatings evolve. Drivers for change are varied and these can include: regulatory controls to reduce VOC emissions, concerns about toxic hazards of coating raw materials, a desire for cost reduction, commitments to sustainability, and a need for increased product effectiveness.

UV nail gel coatings have gained rapid popularity with fashion conscious individuals who apply nail polish to fingernails or toenails to decorate and protect nail plates. UV nail gels can produce coatings that exhibit phenomenal chip resistance and durability when properly applied and cured in comparison to those nail coatings derived from traditional solvent based nail lacquers. The performance difference particularly becomes apparent when the coating is applied on human finger nails and tested for durability. UV nail gel coatings can easily last for two weeks or more and still look like new whereas conventional nail polishes are easily scratched and will chip or peel from the natural nail in one to five days. UV nail gels are typically based on acrylates that cure quickly into dense, crosslinked thermoset coatings within half a minute or so. This is an advantage as the coating becomes almost immediately resistant to denting and scratching. Conventional nail lacquers show significant sensitivity to denting while the solvent evaporates from the coating and this requires great care by the individual as the coating dries and hardens; a process that can take easily fifteen to twenty minutes. However, conventional nail polish is easily removed with solvent whereas it can take some effort to remove a fully cured UV nail gel from the nail surface. An expensive UV light also is required for UV nail gel application and this has limited the success of UV nail gels in the mass market for home use. The expense of a UV light is less of an issue for professional salons where a right balance between service rate and a customers' perception of service is more important. As such, there is a need in the consumer market place for durable nail coatings that can cure quickly but do not require procurement of an UV light.

Highly crosslinked, durable coating compositions can be achieved using Michael addition chemistry. The Michael addition reaction involves the nucleophilic addition of a Michael donor, such as a carbanion or another nucleophile to a Michael acceptor, such as an α,β-unsaturated carbonyl. As such, the base catalyzed addition of activated methylene moieties to electron deficient C=C double bonds are known in coatings applications. Representative examples of suitable materials that can provide activated methylene or methine groups are generally disclosed in U.S. Pat. No. 4,871,822, which resins contain a methylene and/or mono-substituted methylene group in the alpha-position to two activating groups such as, for example, carbonyl, cyano, sulfoxide and/or nitro groups. Preferred are resins containing a methylene group in the alpha-position to two carbonyl groups, such as malonate and/or acetoacetate group-containing materials, malonates being most preferred. The α,β-unsaturated carbonyl typically is an acrylate material and representative materials have been disclosed in U.S. Pat. No. 4,602,061. The Michael reaction is fast, can be carried out at ambient temperatures and gives a chemically stable crosslinking bond without forming any reaction by-product.

A typical crosslinkable coating composition comprises a resin ingredient A (Michael donor), a resin ingredient B (Michael acceptor) and a base to start and catalyze the Michael addition reaction. The base catalyst should be strong enough to abstract, i.e. activate a proton from resin ingredient A to form the Michael donor carbanion species. Since the Michael addition cure chemistry can be very fast, the coating formulator is challenged to control the speed of the reaction to achieve an acceptable balance of pot life, open time, tack free time and cure time. Pot life is defined as the amount of time during which the viscosity of a mixed reactive system doubles. Working life or working time informs the user how much time they have to work with a reactive two part system before it reaches such a high state of viscosity, or other condition, that it cannot be properly worked with to produce an acceptable application result. Gel time is the amount of time it takes for a mixed, reactive resin system to gel or become so highly viscous that it has lost fluidity. The open time of a coating is a practical measure of how much time it takes for a drying or curing coating to reach a stage where it can no longer be touched by brush or roller when applying additional coating material without leaving an indication that the drying or curing coating and newly applied coating did not quite flow together. These indications normally take the form of brush or roller marks and sometimes a noticeable difference in sheen levels. The tack free time is the amount of time it takes for a curing or drying coating to be no longer sticky to the touch, i.e. the time for a system to become hard to the touch, with no tackiness. Cure time is the amount of time it takes for a coating system to reach full final properties.

The Michael reaction starts the very moment when coating resin ingredients A and B are mixed together with a suitable base. Since it is a fast reaction, the material in a mixing pot starts to crosslink and the fluid viscosity starts to rise. This limits the pot life, working time and general use as a coating. A dormant initiator that is essentially passive while coating material remains in a mixing vessel but that activates the Michael addition reaction upon film formation allows for longer pot life and working time, yet would show good open time, tack free time and cure time. Hence, the application of dormant initiator technology can provide the formulator with tools to control the speed of the reaction in order to achieve desirable cure characteristics.

U.S. Pat. No. 8,962,725 describes a blocked base catalyst for Michael addition, which is based on substituted carbonate salts. Preferred Michael donor resins are based on malonate and Michael acceptor resins are acrylates. The substituted carbonates can bear substituents, but these should not substantially interfere with the crosslinking reaction between malonate and acrylate. The carbonate salts release carbon dioxide and a strong base upon activation by means of film formation. The base is either hydroxide or alkoxide. Before practical pot life and gel times are achieved with acceptable curing characteristics, the carbonate requires presence of a certain amount of water in the coating formulation for the blocking of the base to become effective. All disclosed blocked carbonate examples utilize methanol and/or water. However, malonate esters are known to be susceptible to base hydrolysis, particularly when water is present. Hence, the water necessary to block the carbonate base can thus degrade malonate oligomers or polymers at the same time, which in turn can lead to altered coatings performance. The hydrolysis product furthermore can result in undesirable destruction of base catalyst by means of formation of malonate salt; a reaction which is cloaked as longer pot life and gel time. Presence of water can also be quite problematic in certain coatings applications. Wood grain raising is a significant problem when water is present in wood coatings; water penetrates into wood, which causes swelling and lifting of fibers and this leaves a rough surface. Water also can cause flash rust, i.e. appearance of rust spots on a metal surface during drying of newly applied paint that contains water. Longer term rust formation in terms of corrosion may also be a problem when dealing with formulations that contain water.

SUMMARY OF THE INVENTION

In one embodiment, the present invention provides for a crosslinkable coating composition comprising: ingredient A that has at least two protons that can be activated to form a Michael carbanion donor; ingredient B that functions as a Michael acceptor having at least two ethylenically unsaturated functionalities each activated by an electron-withdrawing group; and a dormant carbamate initiator of Formula (1)

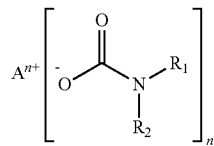

wherein $R_1$ and $R_2$ can be independently selected from hydrogen, a linear or branched substituted or unsubstituted alkyl group having 1 to 22 carbon atoms; 1 to 8 carbon atoms; and $A^{n+}$ is a cationic species or polymer and n is an integer equal or greater than 1 with the proviso that $A^{n+}$ is not an acidic hydrogen; and optionally further comprising ammonium carbamate ($H_2NR_1R_2^{+-}OC=ONR_1R_2$). In one such embodiment, the dormant carbamate initiator initiates Michael Addition to achieve cross linking when the crosslinkable coating composition is applied to a surface.

In another embodiment, the present invention provides for the crosslinkable coating composition wherein ingredient A is selected from the group consisting of compounds, oligomers or polymers. In one such embodiment, the present invention provides for crosslinkable coating composition wherein the ingredient A is independently selected from a malonate group containing compound, a malonate group containing oligomer, a malonate group containing polymer, an acetoacetate group containing compound, an acetoacetate group containing oligomer, an acetoacetate group containing polymer or combinations thereof.

In one such embodiment, the present invention provides for the crosslinkable coating composition wherein the malonate group containing compound, malonate group containing oligomer, malonate group containing polymer, an acetoacetate group containing compound, acetoacetate group containing oligomer, or acetoacetate group containing polymer are each selected from the group consisting of: polyurethanes, polyesters, polyacrylates, epoxy polymers, polyamides, polyesteramides or polyvinyl polymers, wherein such compounds, oligomers or polymers have (i) a malonate group; (ii) an acetoacetate group or (iii) combinations thereof located in a main chain of such compound or oligomer or polymer or a side chain of such compound or oligomer or polymer.

In another embodiment, the present invention provides for the crosslinkable coating composition wherein ingredient B is selected from the group consisting of acrylates, fumarates, maleates and combinations thereof. In one such embodiment, the present invention provides for the crosslinkable coating composition wherein the acrylate is independently selected from the group consisting of hexanediol diacrylate, trimethylolpropane triacrylate, pentaerythritol triacrylate, di-trimethylolpropane tetraacrylate, bis(2-hydroxyethyl acrylate) trimethylhexyl dicarbamate, bis(2-hydroxyethyl acrylate) 1,3,3-trimethylcyclohexyl dicarbamate, bis(2-hydroxyethyl acrylate) methylene dicyclohexyl dicarbamate and combinations thereof.

In one such embodiment, the present invention provides for the crosslinkable coating composition wherein ingredient B is independently selected from polyesters, polyurethanes, polyethers and/or alkyd resins each containing at least two pendant ethylenically unsaturated groups each activated by an electron-withdrawing group.

In one such embodiment, the present invention provides for the crosslinkable coating composition wherein ingredient B is independently selected from the group consisting of polyesters, polyurethanes, polyethers and/or alkyd resins each containing at least one pendant acryloyl functional group.

In another embodiment, the present invention provides for the crosslinkable coating composition further comprising an ingredient D having one or more reactive protons that are more acidic than the protons of ingredient A, with respect to pKa. In one such embodiment, the present invention provides for the crosslinkable coating composition wherein the one or more reactive protons of ingredient D are less acidic than the ammonium cation of the optional ammonium carbamate, with respect to pKa.

In another embodiment, the present invention provides for the crosslinkable coating composition further comprising less than 10 wt. %; 5 wt. %; 1 wt. %; 0.1 wt. %; 0.01 wt. % water. In another embodiment, the present invention provides for the crosslinkable coating composition substantially free of water.

In another embodiment, the present invention provides for the crosslinkable coating composition further comprising an organic solvent. In one such embodiment, the organic solvent is independently selected from an alcohol, ester, ether, glycol ether, ketone, aromatic and combinations thereof. In one such embodiment, the alcohol is independently selected from methanol, ethanol, iso-propanol, butanol, iso-butanol and combinations thereof.

In another embodiment, the present invention provides for the crosslinkable coating composition wherein $A^{+n}$ is a monovalent quaternary ammonium compound of Formula (2)

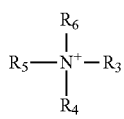

wherein $R_3$, $R_4$ and $R_5$ are independently selected from linear or branched alkyl chains having from 1 to 22 carbon atoms; or 1 to 8 carbon atoms and combinations thereof; and wherein $R_6$ is independently selected from the group consisting of: methyl, an alkyl group having from 2 to 6 carbon atoms or a benzyl group.

In another embodiment, the present invention provides for the crosslinkable coating composition wherein ingredient A, ingredient B and the carbamate initiator are contained in a container having two or more chambers, which are separated from one another. In one such embodiment, ingredient A and ingredient B are contained in separate chambers to inhibit any reaction. In another such embodiment, the carbamate initiator is contained in the chamber having ingredient A, and optionally containing $CO_2$ and/or ammonium carbamate. In another such embodiment, the carbamate initiator is contained in the chamber having ingredient B, and optionally containing $CO_2$ and/or ammonium carbamate.

In another embodiment, the present invention provides for the crosslinkable coating composition such that ingredient A and ingredient B are contained in the same chamber and the carbamate initiator is contained in a separate chamber to inhibit any reaction and said separate chamber optionally containing $CO_2$ and/or ammonium carbamate.

In another embodiment, the present invention provides for the crosslinkable coating composition wherein ingredient A and ingredient B and carbamate initiator are contained in a container having a single chamber, wherein the container optionally independently (i) contains $CO_2$ and/or ammonium carbamate or (ii) contains ammonium carbonate and is filled to capacity with essentially no space remaining for other solid, liquid or gaseous ingredients.

In another embodiment, the present invention provides for a polymerizable nail coating composition comprising the crosslinkable coating composition described herein. In one such embodiment, the polymerizable nail coating composition includes at least one solvent selected from acetone, ethyl acetate, butyl acetate, isopropyl alcohol, ethanol, methyl ethyl ketone, and combinations thereof. In another certain embodiment, the polymerizable nail coating composition further includes one or more of dyes, pigments, effect pigments, phosphorescent pigments, flakes and fillers and combinations thereof. In another certain embodiment, the polymerizable nail coating composition further includes a rheological additive to modify rheology. In another certain embodiment, the polymerizable nail coating composition further includes a wetting agent. In another embodiment, the polymerizable nail coating composition further includes an adhesion promotor. In another certain embodiment, the polymerizable nail coating composition includes nitrocellulose, polyvinylbutyral, tosylamide formaldehyde and/or tosylamide epoxy resins. In another certain embodiment, the polymerizable nail coating composition includes a cellulose acetate alkylate selected from the group consisting of cellulose acetate butyrate, cellulose acetate propionate, and mixtures thereof. In another certain embodiment, the polymerizable nail coating composition includes at least one colorant independently selected from the group consisting of (i) a dye; (ii) an inorganic pigment; (iii) a lake or (iv) combinations thereof.

In another embodiment, the present invention provides for a coating composition comprising the crosslinkable coating composition as described herein.

In another embodiment, the present invention provides for a crosslinkable coating composition comprising: ingredient A that has at least two protons that can be activated to form a Michael carbanion donor; ingredient B that functions as a Michael acceptor having at least two ethylenically unsaturated functionalities each activated by an electron-withdrawing group; and ingredient C, which is a dormant carbamate initiator system formed from: a: ammonium carbamate salt derived from the reaction of: a1: carbon dioxide a2: one or more polyamines a3: optionally one or more monoamines b: such ammonium carbamate salt being subsequently treated with base, ion exchange or other chemical means so that at least part of the protonated ammonium cations have been replaced by $A''^{n+}$, and where $A''^{n+}$ is a cationic species or polymer and n is an integer equal or greater than 1 with the proviso that $A''^{n+}$ is not hydrogen.

DETAILED DESCRIPTION

The invention disclosed here is a crosslinkable composition comprising a resin ingredient A (Michael donor), a resin ingredient B (Michael acceptor) and a dormant carbamate initiator ingredient C. The invention generally is useful as a decorative and/or functional coating, and the invention particularly is useful as a coating for human finger nails or toe nails.

Resin ingredient A (Michael donor): Resin ingredients A are compounds, oligomers or polymers that contain functional groups that have reactive protons that can be activated to produce a carbanion Michael donor. In one embodiment, the functional group can be a methylene or methine group and resins have been described in U.S. Pat. Nos. 4,602,061 and 8,962,725 for example. In one embodiment, resin ingredients A are those derived from malonic acid or malonate esters, i.e. malonate. Oligomeric or polymeric malonate compounds include polyurethanes, polyesters, polyacrylates, epoxy resins, polyamides, polyesteramides or polyvinyl resins each containing malonate groups, either in the main chain or the side chain or in both.

In one embodiment, polyurethanes having malonate groups may be obtained, for instance, by bringing a polyisocyanate into reaction with a hydroxyl group containing ester or polyester of a polyol and malonic acid/malonates, by esterification or transesterification of a hydroxyl functional polyurethane with malonic acid and/or a dialkyl malonate. Examples of polyisocyanates include hexamethylenediisocyanate, trimethylhexamethylene diisocyanate, isophorone diisocyanate, toluene diisocyanate and addition products of a polyol with a diisocyanate, such as that of trimethylolpropane to hexamethylene diisocyanate. In one embodiment, the polyisocyanate is selected from isophorone diisocyanate and trimethylhexamethylene diisocyanate. In another embodiment, the polyisocyanate is isophorone diisocyanate. In some embodiments, hydroxyl functional polyurethanes include the addition products of a polyisocyanate, such as the foregoing polyisocyanates, with di- or polyvalent hydroxyl compounds, including diethyleneglycol, neopentyl glycol, dimethylol cyclohexane, trimethylolpropane, 1,3-propanediol, 1,4-butanediol, 1,6-hexanediol and polyether polyols, polyester polyols or polyacrylate polyols. In some embodiments, the di- or polyvalent hydroxyl compounds include diethyleneglycol, 1,3-propanediol, 1,4-butanediol and 1,6-hexanediol. In other embodiments, the di- or polyvalent hydroxyl compounds include diethyleneglycol and 1,6-hexanediol.

In one embodiment, malonic polyesters may be obtained, for instance, by polycondensation of malonic acid, an alkylmalonic acid, such as ethylmalonic acid, a mono- or dialkyl ester of such a carboxylic acid, or the reaction product of a malonic ester and an alkylacrylate or methacrylate, optionally mixed with other di- or polycarboxylic with one or more dihydroxy and/or polyhydroxy compounds, in combination or not with mono hydroxyl compounds and/or carboxyl compounds. In some embodiments, polyhydroxy compounds include compounds containing 2-6 hydroxy group and 2-20 carbon atoms, such as ethylene glycol, diethyleneglycol, propylene glycol, trimethylol ethane, trimethylolpropane, glycerol, pentaerythritol, 1,4-butanediol, 1,6-hexanediol, cyclohexanedimethanol, 1,12-dodecanediol and sorbitol. In some embodiments, the polyhydroxy compounds include diethylene glycol, propylene glycol, 1,4-butanediol and 1,6-hexanediol. In other embodiments, the polyhydroxyl compounds include propylene glycol and 1,6-hexanediol. In certain embodiments, the polyhydroxy may be a primary alcohol and in certain other embodiments, the polyhydroxy may be a secondary alcohol. Examples of polyols with secondary alcohol groups are 2,3-butanediol, 2,4-pentanediol and 2,5-hexanediol and the like.

In one embodiment, malonate group-containing polymers also may be prepared by transesterification of an excess of dialkyl malonate with a hydroxyl functional polymer, such as a vinyl alcohol-styrene copolymer. In this way, polymers with malonate groups in the side chains are formed. After the reaction, the excess of dialkyl malonate may optionally be removed under reduced pressure or be used as reactive solvent.

In one embodiment, malonate group or acetoacetate group containing polymers may also be obtained from reaction with malonate or acetoacetonate with polyols, such as those polyols that are commercially sold for reaction with isocyanates to form polyurethane coatings.

In one embodiment, malonic epoxy esters may be prepared by esterifying an epoxy polymer with malonic acid or a malonic monoester, or by transesterifying with a dialkylmalonate, optionally in the presence of one or more other carboxylic acids or derivatives thereof.

In one embodiment, polyamides having malonate groups may be obtained in the same manner as polyesters, at least part of the hydroxyl compound(s) being replaced with a mono- or polyvalent primary and/or secondary amine, such as cyclohexylamine, ethylene diamine, isophorone diamine, hexamethylene diamine, or diethylene triamine.

In some embodiments, such polyamide compounds can be obtained when 12-hydroxystearic acid is reacted with a diamine such as ethylenediamine. Such polyamides have secondary alcohol groups, which can be esterified with malonic acid or malonate in a second reaction step. In some embodiments, other diamines may also be used in the reaction with 12-hydroxystearic acid, for example: xylylenediamine, butylenediamine, hexamethylenediamine, dodecamethylenediamine, and even dimer amine, which is derived from dimer acid. Polyamines may also be used, but in a right stoichiometric ratio as to avoid gelling of the polyamide in the reactor. Lesquerolic acid may also be used in reactions with polyamines to yield polyamides bearing secondary alcohol groups, which can be used in reactions with malonate to form malonate containing compounds. Reactions that yield malonamides are much less desirable.

In some embodiments, the above mentioned malonate resins may be blended together to achieve optimized coatings properties. Such blends can be mixtures of malonate modified polyurethanes, polyesters, polyacrylates, epoxy resins, polyamides, polyesteramides and the like, but mixtures can also be prepared by blending various malonate modified polyesters together. In some other embodiments, various malonate modified polyurethanes can be mixed together, or various malonate modified polyacrylates, or malonate modified epoxy resins, or various malonate modified polyamides, malonate modified polyesteramides.

In certain embodiments, malonate resins are malonate group containing oligomeric esters, polyesters, polyurethanes, or epoxy esters having 1-100, or 2-20 malonate groups per molecule. In some such embodiments, the malonate resins should have a number average molecular weight in the range of from 250 to 10,000 and an acid number not higher than 5, or not higher than 2. Use may optionally be made of malonate compounds in which the malonic acid structural unit is cyclized by formaldehyde, acetaldehyde, acetone or cyclohexanone. In some embodiments, molecular weight control may be achieved by the use of end capping agents, typically monofunctional alcohol, monocarboxylic acid or esters. In one embodiment, malonate compounds may be end capped with one or more of 1-hexanol, 1-octanol, 1-dodecanol, hexanoic acid or its ester, octanoic acid or its esters, dodecanoic acid or its esters, diethyleneglycol monoethyl ether, trimethylhexanol, and t-butyl acetoacetate, ethyl acetoacetate. In one such embodiment, the malonate is end capped with 1-octanol, diethyleneglycol monoethyl ether, trimethylhexanol, t-butyl acetoacetate and ethyl acetoacetate. In another such embodiment, the malonate is end capped t-butyl acetoacetate, ethyl acetoacetate and combinations thereof.

Monomeric malonates may optionally be used as reactive diluents, but certain performance requirements may necessitate removal of monomeric malonates from resin ingredient A.

In some embodiments, resin ingredients A include oligomeric and/or polymeric acetoacetate group-containing resins. In some embodiments, such acetoacetate group-containing resins are acetoacetic esters as disclosed in U.S. Pat. No. 2,759,913, diacetoacetate resins as disclosed in U.S. Pat. No. 4,217,396 and acetoacetate group-containing oligomeric and polymeric resins as disclosed in U.S. Pat. No. 4,408,018. In some embodiments, acetoacetate group-containing oligomeric and polymeric resins can be obtained, for example, from polyalcohols and/or hydroxyl-functional polyether, polyester, polyacrylate, vinyl and epoxy oligomers and polymers by reaction with diketene or transesterication with an alkyl acetoacetate. Such resins may also be obtained by copolymerization of an acetoacetate functional (meth) acrylic monomer with other vinyl- and/or acrylic-functional monomers. In certain other embodiments, the acetoacetate group-containing resins for use with the present invention are the acetoacetate group-containing oligomers and polymers containing at least 1, or 2-10, acetoacetate groups. In some such embodiments, such acetoacetate group containing resins should have Mn in the range of from about 100 to about 5000 g/mol, and an acid number of about 2 or less. Resins containing both malonate and acetoacetate groups in the same molecule may also be used.

In another embodiment, the above mentioned malonate group containing resins and acetoacetate group-containing resins may also be blended to optimize coatings properties as desired, often determined by the intended end application.

Structural changes at the acidic site of malonate or acetoacetate can alter the acidity of these materials and derivatives thereof. For instance, pKa measurements in DMSO show that diethyl methylmalonate (MeCH(CO$_2$Et)$_2$) has a pKa of 18.7 and diethyl ethylmalonate (EtCH(CO$_2$Et)$_2$) has a pKa of 19.1 whereas diethyl malonate (CH$_2$(CO$_2$Et)$_2$) has a pKa of 16.4. Resin ingredient A may contain such substituted moieties and therewith show changes in gel time, open time, cure time and the like. For example, resin ingredient A may be a polyester derived from a polyol, diethyl malonate and diethyl ethylmalonate.

Resin ingredient B (Michael acceptor): Resin ingredients B (Michael acceptor) generally can be materials with ethylenically unsaturated moieties in which the carbon-carbon double bond is activated by an electron-withdrawing group, e.g. a carbonyl group in the alpha-position. In some embodiments, resin ingredients B are described in: U.S. Pat. Nos. 2,759,913, 4,871,822, 4,602,061, 4,408,018, 4,217,396 and 8,962,725. In certain embodiments, resin ingredients B include acrylates, fumarates and maleates. In other certain embodiments, resin ingredient B is an unsaturated acryloyl functional resin.

In some embodiments, resin ingredients B are the acrylic esters of chemicals containing 2-6 hydroxyl groups and 2-20 carbon atoms. These esters may optionally contain hydroxyl groups. In some such embodiments, examples of such acrylic esters include hexanediol diacrylate, trimethylolpropane triacrylate, pentaerythritol triacrylate, di-trimethylolpropane tetraacrylate. In one such embodiment, acrylic esters include trimethylolpropane triacrylate, di-trimethylolpropane tetraacrylate, dipentaerythritol hexaacrylate, pentaerythritol ethoxylated (EO)$_n$ tetraacrylate, trimethylolpropane ethoxylated (EO)$_n$ triacrylate and combinations thereof. In another embodiment, acrylamides may be used as a resin ingredient B.

In other embodiments, resin ingredients B are polyesters based upon maleic, fumaric and/or itaconic acid (and maleic and itaconic anhydride), and chemicals with di- or polyvalent hydroxyl groups, optionally including materials with a monovalent hydroxyl and/or carboxyl functionality.

In other embodiments, resin ingredients B are resins such as polyesters, polyurethanes, polyethers and/or alkyd resins containing pendant activated unsaturated groups. These include, for example, urethane acrylates obtained by reaction of a polyisocyanate with an hydroxyl group-containing acrylic ester, e.g., an hydroxyalkyl ester of acrylic acid or a resins prepared by esterification of a polyhydroxyl material with acrylic acid; polyether acrylates obtained by esterification of an hydroxyl group-containing polyether with acrylic acid; polyfunctional acrylates obtained by reaction of an hydroxyalkyl acrylate with a polycarboxylic acid and/or a polyamino resin; polyacrylates obtained by reaction of acrylic acid with an epoxy resin; and polyalkylmaleates obtained by reaction of a monoalkylmaleate ester with an epoxy polymer and/or an hydroxyl functional oligomer or polymer. In certain embodiments, polyurethane acrylate resins may be prepared by reaction of hydroxyalkyl acrylate with polyisocyanate. Such polyurethane acrylate resins independently include bis(2-hydroxyethyl acrylate) trimethylhexyl dicarbamate [2-hydroxyethyl acrylate trimethylhexamethylene diisocyanate (TMDI) adduct], bis(2-hydroxyethyl acrylate) 1,3,3-trimethylcyclohexyl dicarbamate [2-hydroxyethyl acrylate 1,3,3-trimethylcyclohexyl diisocyanate/isophorone diisocyanate (IPDI) adduct], bis(2-hydroxylethyl acrylate) hexyl dicarbamate [2-hydroxyethyl acrylate hexamethylene diisocyanate (HDI) adduct], bis(2-hydroxylethyl acrylate) methylene dicyclohexyl dicarbamate [2-hydroxyethyl acrylate methylene dicyclohexyl diisocyanate (HMDI) adduct], bis(2-hydroxyethyl acrylate) methylenediphenyl dicarbamate [2-hydroxyethylacrylate methylenediphenyl diisocyanate (MDI) adduct], bis(4-hydroxybutyl acrylate) 1,3,3-trimethylcyclohexyl dicarbamate [4-hydroxybutyl acrylate IPDI adduct], bis(4-hydroxybutyl acrylate) trimethylhexyl dicarbamate [4-hydroxybutyl acrylate TMDI adduct], bis(4-hydroxybutyl acrylate) hexyl dicarbamate [4-hydroxybutyl acrylate HDI adduct], bis(4-hydroxybutyl acrylate) methylene dicyclohexyl dicarbamate [4-hydroxybutyl acrylate HMDI adduct], bis(4-hydroxybutyl acrylate) methylenediphenyl dicarbamate [4-hydroxybutyl acrylate MDI adduct].

In other embodiments, resin ingredients B have unsaturated acryloyl functional groups.

In certain embodiments, the acid value of the activated unsaturated group-containing material (resin ingredient B) is sufficiently low to not substantially impair the Michael addition reaction, for example less than about 2, and further for example less than 1 mg KOH/g.

As exemplified by the previously incorporated references, these and other activated unsaturated group containing resins, and their methods of production, are generally known to those skilled in the art, and need no further explanation here. In certain embodiments, the number of reactive unsaturated group ranges from 2 to 20, the equivalent molecular weight (EQW: average molecular weight per reactive functional group) ranges from 100 to 2000, and the number average molecular weight Mn ranges from 100 to 5000.

In one embodiment, the reactive part of resin ingredients A and B can also be combined in one A-B type molecule. In this embodiment of the crosslinkable composition both the methylene and/or methine features as well as the α,β-unsaturated carbonyl are present in the same molecule, be it a monomer, oligomer or polymer. Mixtures of such A-B type molecules with ingredient A and B are also useful.

Each of the foregoing embodiments of resin ingredient A and resin ingredient B may be combined with the various embodiments of a dormant carbamate initiator ingredient C, described below, to arrive at the inventions described herein. In one embodiment, resin ingredient A is a polyester malonate composition and resin ingredient B is a polyester acrylate. In another embodiment, resin ingredient A is a polyurethane malonate composition and resin ingredient B is a polyester acrylate. In another embodiment, resin ingredient A is a polyurethane malonate composition and resin ingredient B is a polyester acrylate. In another embodiment, resin ingredient A is a polyurethane malonate composition and resin ingredient B is a polyurethane acrylate. In another embodiment, resin ingredient A is a polyester malonate having acetoacetate end groups and resin ingredient B is a polyester acrylate. In yet another embodiment, resin ingredient A is a polyester malonate having acetoacetate end groups and resin ingredient B is a polyurethane acrylate. In still yet another embodiment, resin ingredient A is a polyester malonate having acetoacetate end groups and resin ingredient B is a mixture of polyester acrylate and polyurethane acrylate.

In the foregoing embodiments, the number of reactive protons for resin ingredients A, and the number of α,β-unsaturated carbonyl moieties on resin ingredient B can be utilized to express desirable ratios and ranges for resin ingredients A and B. Typically, the mole ratio of reactive protons of ingredient A that can be activated with subsequent carbanion formation relative to the activated unsaturated groups on ingredient B is in the range between 10/1 and 0.1/1, or between 4/1 and 0.25/1, or between 3.3/1 and 0.67/1. However, the optimal amount strongly depends also on the number of reactive groups present on ingredients A and/or B.

The amount of dormant carbamate initiator used, expressed as mole ratio of protons that can be abstracted to form an activated Michael donor species (e.g. the methylene group of malonate can provide two protons for reactions, while a methine group can provide one proton to form an activated species) relative to initiator, ranges from about 1000/1 to 1/1, or from 250/1 to 10/1, or from 125/1 to 20/1 but the optimal amount to be used depends also on the amount of solvent present, reactivity of various acidic protons present on resin ingredients A and/or B.

Dormant carbamate initiator ingredient C: Ingredient C is a dormant carbamate initiator with a structure shown in Formula 1:

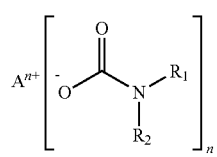

Formula 1

$R_1$ and $R_2$ can be independently selected and is hydrogen or an alkyl group with 1 to 22 carbon atoms where the alkyl group can be linear or branched. In some embodiments, the alkyl group has 1 to 8 carbon atoms or the alkyl group has 1 to 4 carbon atoms. In some such embodiments, the alkyl group is selected from a methyl group, ethyl group, propyl group, butyl group and combinations thereof. In certain embodiments, the alkyl groups are unsubstituted alkyl groups. In other embodiments, the alkyl group can be substituted. In certain embodiments, both $R_1$ and $R_1$ are substituted with hydroxyl groups. $A^{n+}$ is a cationic material and n is an integer equal or greater than 1, with the proviso that $A^{n+}$ is not an acidic hydrogen. In some embodiments, $A^{n+}$ can be a monovalent cation, such as an alkali metal, earth alkali metal or another monovalent metal cation, a quaternary ammonium, a sulfonium or a phosphonium compound. In some embodiments, $A^{n+}$ can also be a multivalent metal cation, or a compound bearing more than one quaternary ammonium or phosphonium groups, or can be a cationic polymer. In certain embodiments, $A^{n+}$ is a monovalent quaternary ammonium cation where n is 1. For the various embodiments described herein, dormant carbamate initiator ingredient C is significantly slow in promoting the Michael reaction prior to applying the crosslinkable composition of this invention as a coating so it can be regarded as essentially inactive, or minimally active, while in a container, yet the initiator initiates Michael addition reaction once the coating is applied as a film.

In some embodiments, the dormant carbamate initiator is derived from carbamates, $(H_2NR_1R_2^{+-}OC=ONR_1R_2)$, independently selected from ammonium carbamate, methylammonium methylcarbamate, ethylammonium ethylcarbamate, propylammonium propylcarbamate, isopropylammonium isopropylcarbamate, butylammonium butylcarbamate, isobutylammonium isobutylcarbamate, pentylammonium pentylcarbamate, and hexylammonium hexylcarbamate. In other embodiments, the dormant carbamate initiator is derived from carbamates independently selected from dimethylammonium dimethylcarbamate, diethylammonium diethylcarbamate, dipropylammonium dipropylcarbamate, dibutylammonium dibutylcarbamate, diisobutylammonium diisobutylcarbamate, dipentylammonium dipentylcarbamate, dihexylammonium dihexylcarbamate, and dibenzylammonium dibenzylcarbamate. In other embodiments, the dormant carbamate initiator is derived from carbamates independently selected from N-methylethylammonium methylethylcarbamate, N-methylpropylammonium methylpropylcarbamate, and N-methylbenzylammonium methylbenzylcarbamate. In some certain embodiments, the dormant carbamate initiator is derived from carbamates independently selected from dimethylammonium dimethylcarbamate, diethylammonium diethylcarbamate, dipropylammonium dipropylcarbamate, N-methylethylammonium methylethylcarbamate, and N-methylpropylammonium methylpropylcarbamate.

For the various embodiments of dormant carbamate initiator, described herein, the dormant carbamate initiator releases carbon dioxide and ammonia or an amine upon activating resin ingredient A by means of a shift in equilibrium. The invention is not meant to be limited by theory however, the overall activation equilibrium reaction can be envisioned as illustrated in equation 1 for example with a malonate material (R' and R" can be the same or different and can be an alkyl or a malonate containing polymer). The activation process produces the carbanion Michael donor.

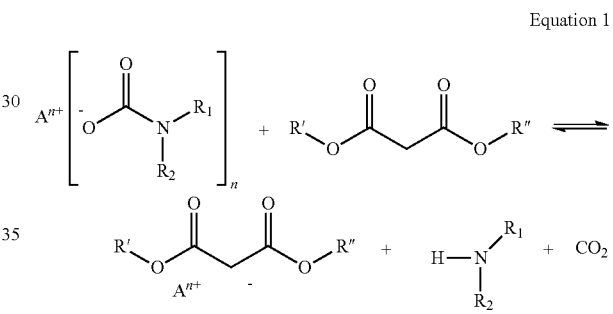

Equation 1

The carbanion can react with the Michael acceptor, an acrylate for example, to yield a malonate-acrylate adduct, which is very basic and is readily protonated, typically by another malonate methylene or methine moiety thus restarting another cycle and continuing the Michael addition process. Solvent potentially can participate in the Michael addition cycle. The equilibrium of equation 1 can be shifted according to Le Châtelier's principle when ammonia or amine and carbon dioxide are allowed to leave the system therewith unleashing the Michael addition reaction. However, the carbon dioxide and the ammonia or amine that are formed in equation 1 react exothermally with each other at a fast rate to form an ammonium carbamate in an equilibrium reaction that favors formation of the ammonium carbamate. This equilibrium reaction is shown in equation 2.

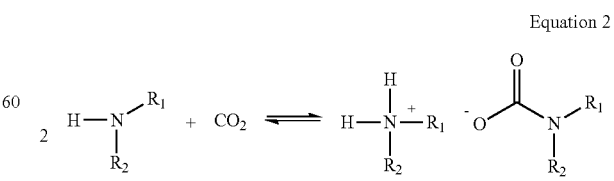

Equation 2

The protonated ammonium cation is a more acidic species ($pK_a \approx 9$) than the malonate methylene group ($pK_a \approx 13$) and reacts with a carbanion such as the malonate-acrylate adduct or the Michael donor carbanion of ingredient A for example. Unless indicated otherwise, the pKa values described herein are defined on an aqueous basis. The initial carbamate initiator reforms in this reaction step. This process is illustrated in equation 3, where [Mal-Ac] is the malonate acrylate adduct.

Equation 3

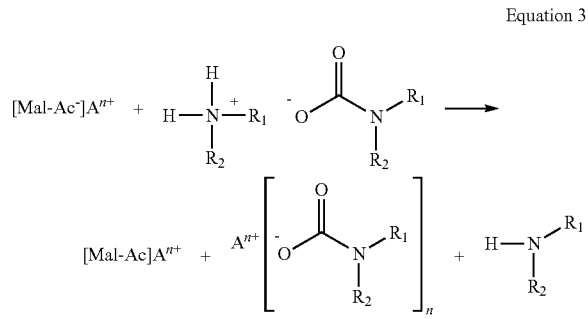

The dormant carbamate initiator thus is able to start the Michael addition cycle by means of a shift in equilibrium, but its decomposition products push back on the equilibrium and can react and stop the Michael reaction and regenerate the dormant carbamate initiator as long as amine and carbon dioxide are available. This ensures long pot life and gel time of the coating composition. Once the coating composition is applied on a substrate, the amine and carbon dioxide can escape into the atmosphere above the coating film and therewith unleash the full speed potential of the Michael addition reaction.

Only ammonia, primary and secondary amines can react with carbon dioxide to form ammonium carbamate material. Tertiary amines do not react with carbon dioxide to form carbamates. However, ammonia, and amines can also react with acrylates at ambient conditions albeit at different rates and these competing aza-Michael additions are illustrated in equation 4.

Equation 4

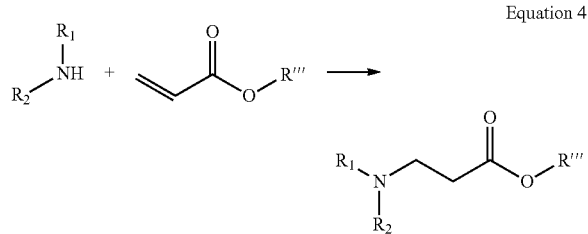

The inventors surprisingly found the carbamate initiator of formula 1 to be dormant in the crosslinkable composition of this invention despite the reaction shown in equation 4, which has the potential to drive a shift in equilibria. The reactions shown in equation 1, 2, 3 and 4 can be utilized to fine tune overall pot life, open time, cure rate and gel time. The reaction shown in equation 4 has an advantage in that it can remove undesirable amine odor from the curing coating as the dormant carbamate initiator activates.

In some embodiments, additional amine functional groups can optionally be added to the coating formulation to impact pot life, open time, cure rate and gel time. In another embodiment, both a quaternary ammonium carbamate, ($A^{+-}OC=ONR_1R_2$), as well as an ammonium carbamate, ($H_2NR_1R_2^{+-}OC=ONR_1R_2$), may be used together as a dormant initiator system. In yet another embodiment, excess carbon dioxide may be utilized to influence equilibria according to Le Châtelier's principle and thus influence pot life, open time, cure time and the like.

Another surprising result of this invention involves the dormant carbamate initiator and its interaction with acetoacetylated resins. Dormancy is preserved despite the fact that amines rapidly react with acetoacetic esters to yield a resin with enamine functionalities. Enamine and ketamines are tautomers. The two isomers readily interconvert with each other, with the equilibrium shifting depending on the polarity of the solvent/environment. Without being bound by theory, it is hypothesized that the enamine and ketamine groups convey increased methine/methylene acidity and the resin can crosslink in a reaction with α,β-unsaturated resins via Michael addition but the reactivity depends on the enamine/ketamine equilibrium. However, once the dormant carbamate initiator actives upon film formation and releases amine and carbon dioxide, the amine may preferentially react with acrylate or acetoacetate moieties in competing reactions, and thus significantly alter the crosslinking reaction characteristics during these initial stages when amine becomes available. The coating formulator thus has additional tools available by making use of the rich reaction chemistry that the amine offers by, for instance, using a mix of acetoacetate and malonate functional groups.

In some embodiments, the crosslinkable composition of this invention contains some solvent. The coating formulator may choose to use an alcohol, or a combination of alcohols as solvent for a variety of reasons. This is not a problem for the carbamate initiator, and regeneration thereof, because ammonia as well as primary and secondary amines react much faster with carbon dioxide than hydroxides or alkoxy anions. Other solvents like ethyl acetate or butyl acetate may also be used, potentially in combination with alcohol solvents. In one embodiment ethanol or Isopropyl alcohol is the solvent. Methanol is not preferred as a solvent because of health and safety risks, and is particularly not preferred and cannot be used when the crosslinkable composition is used as a coating for finger nails and toe nails. Other oxygenated, polar solvents such as ester or ketones for instance, can be used, potentially in combination with alcohol. Other organic solvents may also be used. The crosslinkable composition of this invention may also be formulated without solvent in some cases. The crosslinkable coating contains typically at least 5 wt. % of solvent, or between 5 wt. % and 45 wt. %, or between 5 wt. % and 35 wt. % or not more than 60 wt. % because of VOC restrictions.

In one embodiment, the crosslinkable coating composition further comprising less than 10 wt. %; 5 wt. %; 1 wt. %; 0.1 wt. %; 0.01 wt. % water. In such embodiments, water may be present in the solvent, either deliberately added, or produced in situ in minor quantities during preparation of the dormant initiator. In another embodiment, the crosslinkable coating composition is substantially free of water.

The embodiments of dormant carbamate initiator, described herein, may be prepared in various ways. In one embodiment, the dormant carbamate initiator is prepared by ion exchange. In this embodiment, a cation exchange column is charged with quaternary ammonium ions, which in turn can replace the protonated amine of an ammonium carbamate so that a quaternary ammonium carbamate solution is obtained. In a certain embodiment, a concentrated solution of tributylmethylammonium chloride in water is passed through a cation exchange column. Next, the column is washed free of excess salt and rinsed with anhydrous alcohol to remove any residual water. In a next step, dimethylammonium dimethylcarbamate, $NH_2(CH_3)_2^{+-}OC=ON(CH_3)_2$, optionally diluted with alcohol, is passed through the column so as to obtain a tributylmethylammonium dimethylcarbamate solution in alcohol. A similar approach with anionic ion exchange columns may be devised. The solution can be titrated with base or acid to assess the initiator concentration and whether the dormant initiator formation has been successful. Such analytical reactions are well known to one skilled in the art and need not be further described here.

In another embodiment, an ammonium carbamate solution may be treated with a strong base in alcohol. For example, dimethylammonium dimethylcarbamate is mixed with one molar equivalent of a tetrabutylammonium hydroxide dissolved in ethanol. This yields a tetrabutylammonium dimethylcarbamate solution after the neutralization reaction, as well as dimethyl amine and water. An excess of dimethylammonium dimethylcarbamate may also be used to ensure no residual hydroxide is left in the initiator solution and/or to increase pot life and gel time. In another embodiment, a carbamate such as dimethylammonium dimethylcarbamate may be treated with a quaternary ammonium ethoxide solution in ethanol. This will yield a quaternary ammonium dimethylcarbamate solution in ethanol, dimethylamine but no water is generated during the neutralization step.

In another embodiment, dimethylammonium dimethylcarbamate, is treated with an alcoholic solution of potassium t-butoxide to yield a solution of potassium dimethylcarbamate, dimethylamine and t-butanol.

In another embodiment, a diethyl malonate solution in ethanol is treated with a quaternary ammonium ethoxide prior to adding dimethylammonium dimethylcarbamate to yield a quaternary ammonium dimethylcarbamate solution in ethanol mixed with diethyl malonate and dimethylamine. In yet another embodiment, a quaternary ammonium hydroxide base, such as for instance, tetrabutylammonium hydroxide is added to a solution of diethyl malonate in ethanol. Next, dimethylammonium dimethylcarbamate is added to yield a tetrabutylammonium dimethylcarbamate solution mixed with diethyl malonate, dimethylamine and water. In yet another embodiment, a strong alkoxide base like sodium ethoxide is added to a solution of diethyl malonate in ethanol. Next, a quaternary ammonium chloride salt is added, for instance tributylmethylammonium chloride, and the solution is filtered to remove sodium chloride salt. Next, a stoichiometric amount of dimethylammonium dimethylcarbamate is added to yield a solution of diethyl malonate, tributylmethylammonium carbamate and dimethylamine in ethanol. Malonate resin ingredient A may also be used in such reactions. In a certain embodiment, optionally in the presence of an organic solvent, resin ingredient A is first treated with a quaternary ammonium base, preferably a quaternary ammonium hydroxide solution, before adding an ammonium carbamate, potentially in excess, to yield a mixture of resin ingredient A, quaternary ammonium carbamate and amine.

In yet other embodiments, dialkyl ammonium dialkylcarbamates, or monoalkyl ammonium monoalkylcarbamates or ammonium carbamate or mixtures thereof may also be used but those derived from smaller amines are preferred. Ammonium carbamates are readily prepared by reacting carbon dioxide with ammonia or amine. Mixtures of amines can also be used to prepare ammonium carbamate(s). Carbamate metal salt solutions can also be prepared as described in U.S. Pat. No. 5,808,013.

In certain embodiments, $A'''^+$ of formula 1 is a monovalent quaternary ammonium compound and the structure of this cation is shown in formula 2. A large selection of such quaternary ammonium compounds is commercially available from various manufacturers. In one embodiment, quaternary ammonium compounds are derived from tertiary amines which may be quaternized with a methyl or benzyl group. In one embodiment, tetra alkyl ammonium compounds also can be used. $R_3$, $R_4$ and $R_5$ are independently selected and are linear or branched alkyl chains having from 1 to 22 carbon atoms. In some such embodiments, ammonium compounds where $R_3$, $R_4$ and $R_5$ are independently selected and range from 1 to 8. In some other such embodiments, ammonium compounds can be identified within this group and is dependent upon performance and raw materials costs. In certain embodiments, $R_6$ is a methyl or a benzyl group or an alkyl group having from 1 to 22 carbon atoms or from 2 to 6 carbon atoms. The quaternary ammonium compound is commercially available as a salt and the anion typically is chloride, bromide, methyl sulfate, or hydroxide. Quaternary ammonium compounds with methylcarbonate or ethylcarbonate anions are also available.

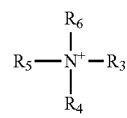

Formula 2

Examples of $A'''^+$ of formula 1 include dim ethyl diethylammonium, dimethyldipropylammonium, triethylmethylammonium, tripropylmethylammonium, tributylmethylammonium, tripentylmethylammonium, trihexylmethylammonium tetraethylammonium, tetrapropylammonium, tetrabutylammonium, tetrapentylammonium, tetrahexylammonium, benzyltrimethylammonium, benzyltriethylammonium, benzyltripropylammonium, benzyltributylammonium, benzyltripentyammonium, benzyltrihexylammonium or combinations thereof.

In another embodiment of the invention, polyamines, potentially in combination with monoamines, may also be utilized as raw material for carbamate formation. In such embodiments, dormant carbamate initiator systems may also be derived from such carbamates when at least a part of the protonated ammonium cations in these ammonium carbamate salts are replaced for quaternary ammonium cations, or other cationic species, or cationic polymers using synthetic approaches described above. For instance, piperazine is known to have a high capacity for carbon dioxide capture and shows a high heat of absorption as well. Piperazine forms various carbamates, e.g. protonated piperazine carbamate, piperazine carbamate and/or piperazine bicarbamate salts with mono or di protonated piperazine. The formation/decomposition equilibrium of carbamates is temperature dependent and varies depending on the amine employed as well as solvent/environment. In another embodiment, carbamates may be derived from pyrrolidine, 2-methylpyrrolidine, 3-methylpyrrolidine, piperidine, piperazine, methylethanolamine, diethanolamine, isopropanolamine, diisopropanolamine.

In yet another embodiment, carbamates may be derived from amines that have a pKa greater than 7, or carbamates derived from amines that have a pKa greater than 8, or carbamates derived from amines that have a pKa greater than 9, or carbamates that are derived from amines that have a pKa greater than 10.

Formulation of Crosslinkable Composition

The crosslinkable composition useful as a coating can be formulated as a one component, a two component system or a three component system. In an embodiment of a two component system, initiator ingredient C is added to a mixture of ingredients A and B just prior to use. In an alternative embodiment, ingredients A and C are mixed, and ingredient B is added prior to use. In yet another embodiment, ingredient A is added to a mixture of ingredients B and C prior to use. The dormant carbamate initiator allows for an opportunity to formulate a three component paint system. In certain embodiments, pot life, working time and gel time can be adjusted by selection of the carbamate structure, the amount used in the crosslinkable composition, presence of additional ammonium carbamate and to a certain extent the amount of solvent and/or water. A gel time of hours, and even days can be readily achieved, and gel times of weeks are possible. In such embodiment of a one component system, ingredients A, B and C are mixed together, optionally with other ingredients to formulate a paint, which is then canned and stored until use. In certain embodiments, a one component system can be enhanced by means of using excess carbon dioxide gas over the crosslinkable composition as to further improve pot life and gel time. For instance, a paint composition formulated according to the invention may have a protective atmosphere of carbon dioxide over the paint volume; and in yet another embodiment, a container containing the crosslinkable composition may even be pressurized with carbon dioxide. In another embodiment, a one component system containing ingredients A, B and C are in a container filled to capacity with essentially no space remaining for other solid, liquid or gaseous ingredients optionally containing ammonium carbamate. In yet another embodiment, additional ammonium carbamate may further enhance stability in such one component coating formulations.

In another embodiment, the present invention provides for the crosslinkable coating composition wherein ingredient A, ingredient B and the carbamate initiator are contained in a container having two or more chambers, which are separated from one another. In one such embodiment, ingredient A and ingredient B are contained in separate chambers to inhibit any reaction. In another such embodiment, the carbamate initiator is contained in the chamber having ingredient A, and optionally containing $CO_2$ and/or ammonium carbamate. In another such embodiment, the carbamate initiator is contained in the chamber having ingredient B, and optionally containing $CO_2$ and/or ammonium carbamate.

In another embodiment, the present invention provides for the crosslinkable coating composition such that ingredient A and ingredient B are contained in the same chamber and the carbamate initiator is contained in a separate chamber to inhibit any reaction and said separate chamber optionally containing $CO_2$ and/or ammonium carbamate.

In another embodiment, the present invention provides for the crosslinkable coating composition wherein ingredient A and ingredient B and carbamate initiator are contained in a container having a single chamber, wherein the container optionally contains $CO_2$ and/or ammonium carbamate.

Malonate esters are known to be susceptible to base hydrolysis, particularly when water is present. Water potentially can lead to undesirable destruction of initiator by means of formation of malonate salt and it can degrade malonate oligomers or polymers, which in turn can lead to altered coatings performance. Transesterification reactions also can occur with malonate esters and alcohol solvent. These reactions potentially can be limiting to the formulation of an acceptable working life, as a coating formulator seeks to increase pot life and gel time for a crosslinkable composition formulated either as a one or two component system. However, primary alcohols such as methanol and ethanol are much more active in transesterification reactions than secondary alcohols such as isopropanol, while tertiary alcohols are generally least active. Furthermore, additional resistance towards hydrolysis and transesterification can be obtained when malonate polyester resins are derived from malonic acid, or a dialkyl malonate such as diethyl malonate, and polyols bearing secondary alcohol groups; such as 2,3-butanediol, 2,4-pentanediol and 2,5-hexanediol and the like. The combination of such polyester resins and non-primary alcohol solvents, such as isopropanol or isobutanol, is particularly useful in achieving desirable resistance towards transesterification reactions. In a certain embodiment, resin ingredient A comprises malonate moieties that have been esterified with polyols bearing secondary alcohol groups and where secondary alcohol is present as solvent in the crosslinkable composition of this invention. In yet another embodiment, tertiary alcohols are used as solvent or solvents as used that do not participate in transesterification reactions. Other resins may also be formulated using such stabilizing approaches towards resin breakdown and such approaches are well known to one skilled in the art and need not be further described here.

In one embodiment, the crosslinkable composition of this invention comprising ingredients A, B and C may optionally contain an additional ingredient D, which once activated, can react with the Michael acceptor. In one such embodiment, ingredient D has one or more reactive protons that are more reactive, i.e. more acidic than those of ingredient A (the pKa of ingredient D is lower than that of ingredient A) yet not as reactive as ammonium carbamate with respect the pKa. In another embodiment, ingredient D may be more acidic than ammonium carbamate with respect to pKa. In such embodiments, the reactive protons of ingredient D are present at a fraction based on the reactive protons of ingredient A where the fraction ranges from 0 to 0.5, or from 0 to 0.35, or between 0 and 0.15.

Examples of ingredient D include; succinimide, isatine, ethosuximide, phthalimide, 4-nitro-2-methylimidazole, 5,5-dimethylhydantioin, phenol, 1,2,4-triazole, ethylacetoacetate, 1,2,3-triazole, ethyl cyanoacetate, benzotriazole, acetylacetone, benzenesulfonamide, 1,3-cyclohexanedione, nitromethane, nitroethane, 2-nitropropane, diethyl malonate, 1,2,3-triazole-4,5-dicarboxylic acid ethyl ester, 1,2,4-triazole-3-carboxylic acid ethyl ester, 3-Amino-1,2,4-triazole, 1H-1,2,3-triazole-5-carboxylic acid ethyl ester, 1H-[1,2,3] triazole-4-carbaldehyde, morpholine, purines such as purine, adenine, guanine, hypoxanthine, xanthine, theobromine, caffeine, uric acid and isoguanine; pyrimidines, such as thymine and cytosine; uracil, glycine, ethanimidamide, cysteamine, allantoin, N,N-dimethylglycine, allopurinol, N-methylpyrrolidine, benzeneboronic acid, salicylaldehyde, 3-hydroxybenzaldehyde, 1-naphthol, methylphenidate and Vitamin E.

In certain embodiments, ingredient D can significantly affect the initial cure speed and thus can generate longer open time.

In another embodiments, ingredient D may be incorporated into resin ingredient A. In such an embodiments, substituted succinimides, including hydroxyl group containing succinimide derivatives, 3-hydroxy-2,5-pyrrolidinedione and 3-(hydroxymethyl)-2,5-pyrrolidinedione, or carboxylic acid group containing succinimide derivative, 2,5-dioxo-3-pyrrolidinecarboxylic acid can undergo condensation reactions with either acid/ester groups or hydroxyl groups at the end of resin A polymer chain, where the succinimide moiety will be incorporated into the polymer backbone as end cap.

In yet another embodiment, maleimides can be copolymerized via radical process with acetoacetoxyethyl methacrylate (AAEM) to a copolymer that contains both acetoacetate group and succinimide groups.

In certain embodiments, the crosslinkable coating composition of this invention can comprise one or more pigments, dyes, effect pigments, phosphorescent pigments, flakes and fillers. Metal flake effect pigments may also be used in the crosslinkable coating composition of this invention and this is an advantage over UV curable nail gel coatings as the UV cure process is hindered by such pigments and these metal flakes are therefore typically not used in such long lasting nail coatings.

The crosslinkable coating compositions of this invention may contain one or more of FD&C or D&C dyes, pigments, lakes and combinations thereof. Lakes are colorants where one or more of the FD&C or D&C dyes are adsorbed on a substratum, such as alumina, blanc fixe, gloss white, clay, titanium dioxide, zinc oxide, talc, rosin, aluminum benzoate or calcium carbonate. In certain embodiments, the D&C dye is independently selected from D&C Red No. 30, D&C Red No. 33, D&C Black No. 2, D&C Yellow No. 5, D&C Green No. 5, Annatto, Caramel and combinations thereof. In certain embodiments, the inorganic pigment is selected from the group consisting of red iron oxide; yellow iron oxide; titanium dioxide; brown iron oxide; chromium oxide green; iron blue (ferric ferrocyanide blue); ultramarine blue; ultramarine violet; ultramarine pink; black iron oxide; bismuth oxychloride; aluminum powder; manganese violet; mica; bronze powder; copper powder; guanine and combinations thereof.

In certain embodiments, the crosslinkable coating composition of this invention can comprise other Michael addition reactive and non-reactive resins or polymers, for instance to facilitate adhesion, and/or aid in coating removal. Such removal aids may be solvent-dissolvable compounds, resins, oligomers or polymers, which are dispersed in the polymerized structure and can be easily dissolved by a solvent to facilitate solvent absorption and migration during removal of the coating.

In certain other embodiments, the crosslinkable coating composition of this invention may optionally comprise resins, such as, but not limited to nitrocellulose, polyvinylbutyral tosylamide formaldehyde and/or tosylamide epoxy resins. Such resins may act as film formers, adhesion promoters, and aids to removal. These resins may also qualify as solvent-dissolvable resins. Nonreactive polymers may also be added to the formulation, and compounds such as 1,3-butanediol may optionally be added to alter properties such as gloss.

In some embodiments, the crosslinkable coating composition of this invention can comprise optional additives such as wetting agents, defoamers, rheological control agents, ultraviolet (UV) light stabilizers, dispersing agents, flow and leveling agents, optical brighteners, gloss additives, radical inhibitors, radical initiators, adhesion promotors, plasticizers and combinations thereof.

Nail Coating Compositions

In some embodiments, the crosslinkable composition of this invention formulated as a nail polish may be packaged in a single unit package good for one time use. Such single serve units contain enough coating material to decorate all finger and toe nails. A single use package may contain a nail polish formulated as a one component system where all ingredients are mixed in one chamber, optionally with extra ammonium carbamate and carbon dioxide to push back on the dormant carbamate initiator or in one chamber filled to capacity with essentially no space remaining for other solid, liquid or gaseous ingredients. The single unit package may contain more than one chambers when the nail polish system is formulated as a multi component system, e.g. two chambers when the nail polish is formulated as a two component system, or three chambers when ingredients A, B and C are all kept separate until use. Packages are known where a seal between chambers is broken to allow for materials to be mixed in the merged chambers and a proper ratio of components is maintained by virtue of the design of the package. Flexible packages and more rigid containers such as bottles that have more than one chamber where contents can be mixed upon demand are known and are readily available. Single unit packages may also include a brush for application. In another approach deviating from a single use concept, material may be dispensed from a single chamber (flexible) package that can be resealed. Multi chamber package that utilize plungers are also known and proper mixing of components can be insured by use of a mixing nozzle for instance. Material may be dispensed multiple times provided the time between uses does not exceed the working life of the nail polish in a mixing chamber or if the working life is to be exceeded, the mixing nozzle is removed and the package capped and stored until future use when a new mixing nozzle will be used. Many packaging solutions are available from packaging providers and these are well known to one skilled in the art.

In an embodiment, the crosslinkable coating composition of this invention is particularly useful to decorate finger and toe nails, and can be applied as a three coat nail polish system, with a base coat applied directly on top of the base nail surface, followed by a color coat and finished with a glossy top coat. In another embodiment, the nail polish system is formulated as a two coat system, where a color coat is applied directly on the bare nail surface, and finished with a glossy top coat, but in yet another embodiment, and base coat is applied to the nail surface to provide adhesion for a glossy color coat. Another embodiment to decorate nails is where the crosslinkable coating composition of this invention is used as a single coat system, which has good adhesion to the nail surface, color and gloss all in a one coat system. It is understood that multiple coats can be applied over a same coat for any of these one, two or three coat systems.

The following examples further describe and demonstrate illustrative embodiments within the scope of the present invention. The examples are given solely for illustration and are not to be construed as limitations of this invention as many variations are possible without departing from the spirit and scope thereof.

Example 1

Synthesis of Carbamate Initiator by Means of Ion Exchange.

A glass column fitted with a frit at the bottom was charged with 55 g of Amberlite IR 120 Na cation exchange resin, which was then swollen with distilled water. The resin was then washed 3 times with 200 ml water, and charged with 10 wt. % of tributylmethylammonium chloride (TBMA Cl) in water solution. To maximize the ion exchange, the charging process was repeated three times. The ion exchange efficiency was followed gravimetrically. After charging the resin with tributylmethylammonium (TBMA) cations and washing free of excess TBMA Cl, the resin was made water free by washing it with anhydrous ethanol. Washing was continued until the water content of the wash ethanol fell below 0.07 wt. % as determined by coulometric Karl-Fischer titration. Next, a 10 wt. % solution of dimethylammonium dimethylcarbamate (DMA DMC) in anhydrous ethanol was passed through the charged resin. Not more than 35% of the resin ion exchange capacity was utilized to ensure a complete conversion of DMA DMC. The tributylmethylammonium dimethylcarbamate (TBMA DMC) initiator was characterized by nuclear magnetic resonance (NMR) analysis and Fourier transform infrared spectroscopy (FTIR) and was titrated with acid and base to assess concentration. In a similar manner, TBMA DMC carbamate initiators were prepared in 1-propanol and 2-propanol.

Example 2

Synthesis of Carbamate Initiator by Neutralization of Malonate Carbanion.

To a 250 ml single neck round-bottom flask was charged 5.0 g of diethyl malonate (DEM) and 28.2 g of a 1.0 M solution of potassium t-butoxide in tetrahydrofuran (THF). A white precipitate was immediately observed. At the end of addition, 50.0 g of anhydrous isopropanol was added to the reaction mixture under constant stirring to obtain a homogeneous white suspension. Then 7.36 g of dry TBMA Cl was mixed into the flask, stirring was continued for another 10-15 minutes before 4.19 g of DMA DMC was added. The reaction mixture was continuously stirred at room temperature for one hour, and white suspension was removed by filtration and a clear carbamate initiator solution was obtained free of water.

Example 3

General Synthesis of Carbamate Initiator by Neutralization of Quaternary Ammonium Hydroxide.

Most of the methanol solvent from a 40 g tetrabutylammonium hydroxide (TBA OH) solution in methanol (1 M) was removed with a rotary evaporator. The material was not allowed to become completely dry without solvent as dry quaternary ammonium hydroxide base was susceptible to decomposition. Next, 40 grams of ethanol was added and most of the solvent was again removed. This procedure was repeated at least two more times until the methanol effectively has been replaced as determined by NMR. The solution strength was determined by titration (typically 1.7 mmol base/g solution). Solvent exchange was also carried out to prepare TBA OH solutions in methanol (typical concentration 1.2 mmol/g solution), 1-propanol (typical concentration of 1.1 mmol base/g solution) and TBA OH in 2-propanol (typical concentration of 1.3 mmol base/g solution). Next, about 25 g of TBA OH in ethanol was mixed with DMA DMC in a 1.0:1.1 molar ratio respectively at room temperature and stirred for 1 hour using a magnetic stirrer. The TBA DMC solution in ethanol was light yellow and was characterized by means of acid and base titrations (potentiometric and with indicator), back titrations and NMR. In a similar manner, TBA DMC solutions were prepared in methanol, 1-propanol and 2-propanol. These initiators were designated as initiator II and the alkanol name was used to indicate the alcohol solvent. TBA DMC solutions in the four alcohols were also prepared using a 1.0:1.5 molar ratio of TBA OH and DMA DMC respectively, and these initiators were designated as initiator III and again, the alkanol name was used to indicate the alcohol solvent.

Example 4

General Synthesis of Carbamate Initiator by Neutralization of Quaternary Ammonium Ethoxide.

Tributylmethylammonium chloride (TBMA Cl), 10 g, was dissolved in ethanol and mixed in 1:1 molar ratio with a 20 wt. % solution of potassium ethoxide in ethanol. The mixture was allowed to stir for 30 min, and the precipitate was then removed by centrifugation. The concentration of TBMA ethoxide solution thus obtained was determined potentiometrically by means of titration with 0.1 N HCl solution. The typical concentration of TBMA ethoxide was about 1.1 mmol/g. Next, about 25 g of TBMA ethoxide in ethanol was mixed with DMA DMC in a 1.0:1.1 molar ratio respectively at room temperature and stirred for 1 hour using a magnetic stirrer. The TBMA DMC solution in ethanol was light yellow in color and is characterized by means of acid and base titrations (potentiometric and with indicator) and NMR.

Example 5

General Synthesis of Carbonate Catalyst.

The methanol solvent of TBA OH solution (1 M) in methanol was replaced with ethanol as described in example 3. Next, a precise amount of the TBA OH in solution was mixed with diethyl carbonate (DEtC) in a 1:5 molar ratio respectively and stirred for 1 hour at room temperature using magnetic stirrer. The final clear catalyst solution was analyzed by means of titration and NMR. In a similar manner, clear solutions were obtained in 1-propanol and 2-propanol. A solution made using the TBA OH base in methanol resulted in white precipitate which was removed by centrifuge followed by filtration using 0.45µ syringe filter. In a similar approach, catalyst solutions were prepared in various alcohols using TBA OH and dimethylcarbonate (DMeC). Transesterification reaction products were observed in the NMR for all cases where the carbonate alkyl group was different from the solvent, e.g. ethanol formation was observed when DEtC was added to TBA OH in isopropanol and isopropyl groups associated with carbonates were also observed.

Example 6

Malonate Resin (I) Synthesis.

A 3 liter reactor was charged with 500 g of diethylene glycol (DEG) and 1509 g of diethyl malonate (DEM). The reactor was equipped with a Dean-Stark apparatus, mechanical stirrer, nitrogen flow and heating equipment. The mixture was heated to about 180° C. with stirring under nitrogen atmosphere. During a four hour reaction time, about 450 ml of ethanol was collected. Next, the temperature was reduced to 115° C. and a vacuum distillation was initiated to remove about 246 g of DEM. The final product was a lightly yellow colored liquid with less than 0.15 wt. % of residual DEM as determined by gas chromatography (GC). Gel permeation chromatography (GPC) analysis showed three peak molecular weight of 900, 600 and 400 g/mol and the malonate methylene equivalent molecular weight of 156 g/mol.

Example 7

Malonate Resin (II) Synthesis.

A reactor was charged with 600 g of polyethylene glycol (PEG 300) and 640 g of DEM and the reaction synthesis procedure was followed from example 6. The reaction yielded a total of about 170 ml of ethanol and 118 g of DEM was removed by distillation. Analysis showed that the light yellow product contains less than 0.1 wt. % of DEM, Mn-1000 g/mol and malonate methylene equivalent molecular weight of 292 g/mol.

Example 8

Malonate Resin (III) Synthesis.

A reactor was charged with 30 g of trimethylolpropane (TMP), 107 g of DEM and 17.7 g of tert-butyl acetoacetate (tBAA) and the reaction synthesis procedure was followed from example 6. The reaction resulted in about 25 g of alcohol and 36 g of material was removed by distillation. The light yellow product contains <0.1% of DEM, Mn-2100 g/mol and malonate methylene equivalent molecular weight of 142 g/mol.

Example 9

Malonate Resin (IV) Synthesis.

A reactor was charged with 40 g of glycerol (Gly), 68.71 g of DEM and 69.5 g of tBAA were charged to the reactor and the reaction synthesis procedure was followed from example 6. The reaction resulted in 45 g of alcohol collection and 3 g of material was removed by distillation. The light yellow product contained <0.1% of DEM, Mn-1400 g/mol and malonate methylene equivalent molecular weight of 145 g/mol.

Example 10

Acetoacetate Modified Polyol.

A reactor (500 ml capacity) was charged with 175 g of STEPANPOL® PC-2011-225 (a commercial polyol resin with hydroxyl value of 225 mg of KOH/g of sample), and 133 g of tertiary butyl acetoacetate. The reactor was equipped with Dean-Stark apparatus, mechanical stirrer, nitrogen flow and heating equipment. The mixture was heated to about 180° C. with stirring under nitrogen atmosphere. In four hours, 55 ml of alcohol were collected and no further distillate was obtained. The reaction temperature was lowered to 115° C. and a vacuum distillation resulted in collection of a total 6 g of tertiary butyl acetoacetate. The final product was light yellow colored with methylene equivalent molecular weight of 306 g/mol (calculated based on the theoretical mole ratio and the tertiary butanol and tertiary butyl acetoacetate collected amount).

Example 11

Malonate Resin (V) Synthesis.

A 500 ml reactor was charged with 66.25 g of DEG, 125.0 g of DEM, 40.65 g of 1-octanol and 4-5 drops of titanium (IV) butoxide. The reactor was equipped with a Dean-Stark apparatus, mechanical stirrer, nitrogen flow and heating equipment. The mixture was heated to about 180° C. with stirring under nitrogen atmosphere. During a four hour reaction time, about 80 ml of ethanol were collected. The final product was a slightly yellow liquid with 0.75 wt. % of residual DEM and 0.95% wt. % of residual 1-octanol as determined by GC. GPC analysis showed Mw/Mn (PDI) of 1944/1550 (1.25) in g/mol and a malonate methylene equivalent molecular weight of 205.0 g/mol.

Example 12

Malonate Resin (VI) Synthesis.

A 500 ml reactor was charged with 92 g of 1,6-hexanediol (HD), 150 g of DEM, 52 g of diethylene glycol monoethylether (DEGMEE) and 4-5 drops of titanium (IV) butoxide. The reactor was equipped with a Dean-Stark apparatus, mechanical stirrer, nitrogen flow and heating equipment. The mixture was heated to about 180° C. with stirring under nitrogen atmosphere. During a four hour reaction time, about 110 ml of ethanol were collected. The final product was a lightly yellow colored liquid with less than 0.15 wt. % of residual DEM as determined by GC. GPC analysis showed Mw/Mn (PDI) 2205/1141 (1.93) in g/mol and the malonate methylene equivalent molecular weight of 216 g/mol.

Example 13

Substituted Malonate Resin (VII) Synthesis.

A reactor was charged with 130 g HD, 250 g of diethyl methylmalonate (DEMM), also known as propanedioic acid, 2-methyl-, 1,3-diethyl ester, 74 g of DEGMEE and 4-5 drops of titanium (IV) butoxide. The reaction synthesis procedure was followed from example 12. The reaction yielded a total of about 146 ml of ethanol. Analysis shows that the light yellow product contained less than 0.1 wt. % of DEMM, Mw/Mm (PDI) 2111/1117 (1.89) in g/mol and malonate methylene equivalent molecular weight of 230 g/mol.

Example 14

Substituted Malonate Resin (VIII) Synthesis.

A reactor was charged with 121 g HD, 240 g of diethyl ethylmalonate (DEEM), 68 g of DEGMEE and 4-5 drops of titanium(IV) butoxide. The reaction synthesis procedure was followed from example 12. The reaction yielded a total of about 144 ml of ethanol. The light yellow product contained <0.1% of DEEM, Mw/Mn (PDI) 2894/1450 (2.0) in g/mol and malonate methylene equivalent molecular weight of 244 g/mol.

Example 15

Malonate Resin (IX) Synthesis.

A 500 ml reactor was charged with 118.76 g of 1,3-propanediol (PD), 250.0 g of DEM and 4-5 drops of titanium (IV) butoxide. The reactor was equipped with a Dean-Stark apparatus, mechanical stirrer, nitrogen flow and heating equipment. The mixture was heated to about 180° C. with stirring under nitrogen atmosphere. During a four hour reaction time, about 160 ml of ethanol were collected. The final product was a colorless liquid. GPC analysis showed Mw/Mn (PDI) of 4459/2226 (2.0) in gram/mole and a malonate methylene equivalent molecular weight of 144.12 g/mol.

Example 16

Malonate Resin (X) Synthesis.

A 500 ml reactor was charged with 206.6 g of HD, 280.0 g of DEM and 4-5 drops of titanium (IV) butoxide. The reactor is equipped with a Dean-Stark apparatus, mechanical stirrer, nitrogen flow and heating equipment. The mixture was heated to about 180° C. with stirring under nitrogen atmosphere. During a four hour reaction time, about 180 ml of ethanol were collected. The final product was a lightly yellow colored liquid with less than 0.04 wt. % of residual DEM and less than 1.34 wt % of residual HD as determined by GC. GPC analysis showed Mw/Mn (PDI) of 8399/3366 (2.5) in gram/mole and a malonate methylene equivalent molecular weight of 186.21 g/mol.

Example 17

Malonate Resin (XI) Synthesis.
A 500 ml reactor was charged with 91.85 g of HD, 155.6 g of DEM, 52.14 g of DEGMEE and 4-5 drops of titanium (IV) butoxide. The reactor was equipped with a Dean-Stark apparatus, mechanical stirrer, nitrogen flow and heating equipment. The mixture was heated to about 180° C. with stirring under nitrogen atmosphere. During a four hour reaction time, about 100 ml of ethanol were collected. The final product was a lightly yellow colored liquid with less than 0.05 wt. % of residual DEM as determined by GC. GPC analysis showed Mw/Mn (PDI) of 2320/1616 (1.44) in gram/mole and a malonate methylene equivalent molecular weight of 216.25 g/mol.

Example 18

Malonate Resin (XII) Synthesis.
A 500 ml reactor was charged with 132.81 g of HD, 150.0 g of DEM, 59.26 g of tBAA and 4-5 drops of titanium (IV) butoxide. The reactor was equipped with a Dean-Stark apparatus, mechanical stirrer, nitrogen flow and heating equipment. The mixture was heated to about 180° C. with stirring under nitrogen atmosphere. During a six hour reaction time, about 120 ml of ethanol/t-butanol mixture were collected. The final product was a lightly yellow colored liquid with less than 0.40 wt. % of residual DEM and less than 1.0% wt. % of residual HD as determined by GC, no residual tBAA was detected. GPC analysis showed Mw/Mn (PDI) of 2550/1242 (2.05) in gram/mole and a malonate methylene equivalent molecular weight of 181.93 g/mol.

Example 19

Diurethane Diacrylate (DUDA) Michael Acceptor Crosslinker Synthesis.
A 500 ml capacity reactor was charged with 85 g of 2-hydroxyethyl acrylate (HEA), a few drops of K-Kat 348 catalyst and 60 mg of phenothiazine inhibitor. The reactor was equipped with a Dean-Stark apparatus, mechanical stirrer, nitrogen flow and heating equipment. The mixture was heated to about 50° C. with stirring under nitrogen atmosphere and 81 g of trimethylhexamethylene diisocyanate (TMDI) was added in a dropwise manner. After the addition was completed, the reaction was continued for another hour and excess isocyanate was quenched using ethanol. Residual ethanol was removed under vacuum and a translucent viscous product was collected as bis(2-hydroxyethyl acrylate) trimethylhexyl dicarbamate.

Example 20

Malonate Resin (XIII) Synthesis.
A 500 ml reactor was charged with 149.8 g of PEG 300, 100 g of DEM, 32.5 g of 1-octanol and 4-5 drops of titanium (IV) butoxide. The reactor was equipped with a Dean-Stark apparatus, mechanical stirrer, nitrogen flow and heating equipment. The mixture was heated to about 180° C. with stirring under nitrogen atmosphere. During an eight hour reaction time, about 70 ml of ethanol were collected. The final product was a lightly yellow colored liquid with less than 0.15 wt. % of residual DEM as determined by GC. GPC analysis showed Mw/Mn (PDI) of 4191/2818 (1.49) in gram/mole and a malonate methylene equivalent molecular weight of 360 g/mol.

Coating Testing
Tack free time was evaluated by lightly pressing a gloved index finger periodically onto the coating. The time when visible marks in the film are no longer left by the pressed finger, is then recorded as the tack free time.

Gel time is taken as the amount of time it takes for a mixed, reactive resin system to gel or become so highly viscous that it has lost fluidity. Typically, the various ingredients are charged into a 4 ml vial and closed with headspace volume as constant as possible to allow for comparison and the sample is kept at room temperature and tilted at regular time intervals to determine whether the material still flows. If no flow is observed during tilting, the vial is held upside down and if no further flow occurs the material is gelled.

Gloss was measured using a handheld Micro-Tri-Gloss meter from BYK Instruments. Measurements were taken at 60 degrees in three different locations on the film and the average is reported.

Pencil Hardness testing was performed according to the ISO 15184 test method at ambient laboratory conditions. The pencil hardness rating scale is as follows: [Soft] 9B-8B-7B-6B-5B-4B-3B-2B-B-HB-F-H-2H-3H-4H-5H-6H-7H-8H-9H [Hard].

Acetone removal was determined by placing a cotton ball in the center of the nail polish coating. Acetone was added to the cotton ball until the liquid layer barely showed at the edge of the cotton ball. After starting the test, the cotton ball was briefly lifted to examine the coating integrity below the cotton ball. In order to adjust for the acetone evaporation throughout the test time period, additional acetone was added to the cotton ball to maintain that light liquid layer at the edge of the cotton ball. The time at which the surface integrity became disrupted was determined as the test end point.

Fineness of Grind was evaluated with a Hegman Gauge according to the ASTM D1210 test method.

Film elasticity and resistance to cracking, elongation and/or detachment from metal test panels was tested with a conical Mandrel bend tester. Test panels were prepared by casting a 3 mil film on aluminum substrates and the films are allowed to cure overnight before testing. Panels folded around the cone were visually examined for the cracks of the film. The point at which the cracking stops was marked and the distance from the farthest end of the crack to the small end of the mandrel was measured and results were expressed on a 0 to 100% scale, with 100% showing no cracks or defects.

Both direct and reverse impact were tested with an impact tester, where reverse impact is considered more severe a test than direct impact. The tester consists of a solid base with a guide tube support. The guide tube has a slot to direct a weight that slides inside the guide tube, and graduations are marked along the slot to facilitate readings. Test panels were first prepared by casting a 3 mil film on aluminum substrates, and films were allowed cure overnight before testing. Panels are placed under the punch and the height of the impacter was adjusted until the reading (maximum height) is determined at which film doesn't fail. The result is expressed as percent and calculated by the dividing the maximum height/160.

To test for water blush, 3 mil films were cast on aluminum substrates and cured overnight. A drop of water is applied to the film to yield a spot of about 1-1.5 centimeter in diameter, which is then covered with a beaker and checked after an hour. White marks or swollen films was considered failure.

Brushability time was determined as the length of time between the addition of initiator up to the point when the mixture viscosity increased so much that it became not possible to apply a uniform aesthetically pleasing layer of nail polish using a typical nail polish bottle brush applicator Inventive Example 1

The TBMA DMC solution in ethanol prepared under example 1 was tested as dormant carbamate initiator. In a vial, 1.0 g of the malonate resin prepared under example 6 was mixed with 1.5 g of di-trimethylolpropane tetraacrylate (DTMPTA) and then 1.148 g of the TBMA DMC initiator solution in ethanol was added. The complete formulation was mixed well and then a test film was applied on a glass substrate to test curing behavior. The coating film became tack-free within 5 minutes and the gel time of the material in the vial was longer than 24 hours. The carbamate was a dormant initiator.

Inventive Example 2

A mixture was prepared in a vial combining 1.0 g of the malonate resin prepared under example 6 and 1.27 g of trimethylolpropane triacrylate (TMPTA). Next, 1.3 g of the TBMA DMC carbamate solution prepared in example 2 was added to the vial and the liquid was mixed well. A film was then applied onto a glass slide and the coating became tack free within 5 minutes. No gelation of the material in the vial was observed after three weeks of aging. Another film was prepared of this aged mixture and again the coating cured within 5 minutes. Hence, the carbamate was an effective dormant initiator.

Inventive Example 3

Three TBA DMC solutions in anhydrous ethanol are compared and tested as dormant initiator. Initiator I was a TBA DMC solution in anhydrous ethanol prepared per the cation exchange procedure as set forth in example 1. Initiator II was prepared in example 3 from TBA OH and DMA DMC in a 1.0:1.1 molar ratio, and initiator III was prepared using a 1.0:1.5 molar ratio. A resin mixture was formulated from the malonate resin prepared under example 6 and TMPTA. The molar ratio for malonate methylene CH$_2$ to TMPTA to initiator was 3:2:0.2 respectively. The percent water for the carbamate initiator obtained by means of neutralization was calculated from reaction stoichiometry and is based as percentage of the total crosslinkable formulation. Anhydrous ethanol was added as necessary to arrive at a comparable percent solvent content. The ethanol solvent content is also based on total weight of the crosslinkable formulation. The tack free time of a film applied on a glass substrate was assessed as well as gel time. Data provided in table 1 show that all three carbamate solutions are active as a dormant carbamate initiator and they become effective once the initiator activates by means of film formation.

TABLE 1

| Carbamate initiator | Wt. % Water | Wt. % Ethanol | Tack free time | Gel time |
|---|---|---|---|---|
| I | 0.0 | 32.7 | 140 sec | >72 h |
| II | 0.2 | 31.8 | 140 sec | >72 h |
| III | 0.2 | 31.2 | 120 sec | >72 h |

Inventive Example 4

Initiator II was prepared in example 3 from TBA OH in ethanol, 1-propanol or 2-propanol with TBA OH to DMA DMC in a 1.0:1.1 molar ratio. Initiator III was prepared also in ethanol, 1-propanol or 2-propanol and the TBA OH to DMA DMC molar ratio employed was 1.0:1.5 respectively. The initiators were used either without addition of additional water, or water was added to these initiator solutions to target about 1.2 wt. % water content based as percentage of the final crosslinkable formulation. At 1.2 wt. % water content, there is about 4.5 moles of water per mole of initiator present. Similarly, a 10-15 wt. % alcohol content was targeted based on the final crosslinkable formulation. A resin mixture was formulated from the malonate resin prepared under example 6 and TMPTA. The molar ratio for malonate methylene CH$_2$ to TMPTA to initiator was chosen at 3:2:0.2 respectively. Films were applied on a glass substrate to test for tack free time. Results shown in table 2 indicate that both carbamate initiators are dormant while the formulation remains in the vial, while good activation occurs once a film is applied. The coating formulation in ethanol shows a longer gel time than 1-propanol and 2-propanol for initiator II, but this can be improved by adding a little additional water and solvent. Addition of additional DMA DMC to the carbamate initiator system also improves gel time when initiator II and III are compared but this does not seem to significantly impact tack free time.

TABLE 2

| Carbamate initiator | Solvent | Wt. % Water | Wt. % Solvent | Tack free time | Gel time |
|---|---|---|---|---|---|
| II | Ethanol | 0.3 | 8.3 | 90 sec | >16 h |
| II | 1-propanol | 0.3 | 8.3 | 90 sec | 6-8 h |
| II | 2-propanol | 0.3 | 8.3 | <90 sec | 6-8 h |
| II | Ethanol | 1.2 | 12.9 | 140 sec | >16 h |
| II | 1-propanol | 1.2 | 12.9 | 140 sec | >16 h |
| II | 2-propanol | 1.2 | 12.9 | 140 sec | >16 h |
| III | Ethanol | 0.3 | 9.1 | 90 sec | >24 h |
| III | 1-propanol | 0.3 | 9.1 | 90 sec | >24 h |
| III | 2-propanol | 0.3 | 9.1 | <90 sec | >24 h |
| III | Ethanol | 1.2 | 12.9 | 120 sec | >24 h |
| III | 1-propanol | 1.2 | 12.9 | 120 sec | >24 h |
| III | 2-propanol | 1.2 | 12.9 | 130 sec | >24 h |

Comparative Example 1 (Versus Inventive Example 3 and 4)

Diethyl carbonate derived catalysts were prepared in ethanol, 1-propanol and 2-propanol as per example 5. Water content was fixed at either 0 wt. %, or water was added to the catalyst solutions to target about 1.2 wt. % water content based as percentage of the final crosslinkable formulation. At 1.2 wt. % water content, there is about 4.5 moles of water per mole of blocked base catalyst present. The catalyst solutions were tested as blocked catalyst in a resin mixture formulated from the malonate resin prepared under example 6 and TMPTA using a molar ratio for malonate methylene $CH_2$ to TMPTA to catalyst of 3:2:0.2 respectively, which is similar to inventive examples 3 and 4. Results shown in table 3 indicate that the carbonate solutions are not active as a blocked catalyst in ethanol, 1-propanol or 2-propanol in the absence of water, and even addition of water up to 1 wt. % of the total formulation does not lead to effective blocking of the carbonate base catalyst in these solvents. No tack free time could be measured because the resin-carbonate catalyst mixture polymerized immediately and an instant gel was formed.

TABLE 3

| Carbonate catalyst | Solvent | Wt. % Water | Wt. % Solvent | Tack free time | Gel time |
|---|---|---|---|---|---|
| DEtC | Ethanol | 0.0 | 14.4 | Instant gel | <30 sec |
| DEtC | 1-propanol | 0.0 | 14.4 | Instant gel | <30 sec |
| DEtC | 2-propanol | 0.0 | 14.4 | Instant gel | <30 sec |
| DEtC | Ethanol | 1.2 | 14.3 | Instant gel | <30 sec |
| DEtC | 1-propanol | 1.2 | 14.3 | Instant gel | <30 sec |
| DEtC | 2-propanol | 1.2 | 14.3 | Instant gel | <30 sec |

Comparative Example 2 (Versus Inventive Example 3 and 4)

The experiment of comparative example 1 was repeated except that dimethyl carbonate catalyst solutions were used as prepared per example 5. Results presented in table 4 show that the blocking is not effective in these solvents when water is absent, and even addition of water up to about 1 wt. % of the total formulation does not produce an effective blocking effect.

TABLE 4

| Carbonate catalyst | Solvent | Wt. % Water | Wt. % Solvent | Tack free time | Gel time |
|---|---|---|---|---|---|
| DMeC | Ethanol | 0.0 | 12.9 | Instant gel | <30 sec |
| DMeC | 1-propanol | 0.0 | 12.9 | Instant gel | <30 sec |
| DMeC | 2-propanol | 0.0 | 12.9 | Instant gel | <30 sec |
| DMeC | Ethanol | 1.2 | 12.9 | Instant gel | <30 sec |
| DMeC | 1-propanol | 1.2 | 12.9 | Instant gel | <30 sec |
| DMeC | 2-propanol | 1.2 | 12.9 | Instant gel | 45 sec |

Inventive Example 5

The experiment of inventive example 4 is repeated except methanol is used as solvent for initiator II and III and results are shown in table 5. Both carbamate solutions are effective and carbamate is active as a dormant initiator that activates once the coating formulations is applied as a film.

TABLE 5

| Carbamate initiator | Solvent | Wt. % Water | Wt. % Methanol | Tack free time | Gel time |
|---|---|---|---|---|---|
| II | Methanol | 0.3 | 8.3 | <90 sec | 4 days |
| III | Methanol | 0.3 | 9.1 | <90 sec | >6 days |

Comparative Example 3 (Versus Inventive Example 5)

A similar experiment is carried out as comparative examples 1 and 2 for DEtC and DMeC respectively, except methanol is used as the solvent and results are shown in table 6.

TABLE 6

| Carbonate catalyst | Solvent | Wt. % Water | Wt. % Methanol | Tack free time | Gel time |
|---|---|---|---|---|---|
| DEtC | Methanol | 0.0 | 14.3 | <90 sec | 16 h |
| DEtC | Methanol | 1.2 | 14.3 | <90 sec | 6 days |
| DMeC | Methanol | 0.0 | 13.0 | <90 sec | 16 h |
| DMeC | Methanol | 1.2 | 12.9 | <120 sec | >6 days |

Inventive Example 6

About 1 ml of the initiators prepared in example 1 and example 3 (1:1.1 ratio of TBMA OH to DMA DMC) with as-is concentration is each added to a 2 ml clear vial. DMA DMC is also added to a vial for comparison. The carbamate solutions obtained via ion exchange are essentially free of water, while the carbamate solutions obtained via neutralization as per example 3 contain an equal molar amount of water per amount of initiator. Next, 2 drops of phenolphthalein indicator is added to the solution and mixed well. After mixing, the color is observed and a pink color means the solutions is basic, while a colorless solution means no base is present. The results are shown in Table 7. As expected, the TBMA OH solution has a pink color and is basic, but the carbamate solutions are all colorless. Hence, the dormant carbamate initiator solutions are not basic.

TABLE 7

| Materials | Solvent | Solution color | Comment |
|---|---|---|---|
| DMA DMA | — | Colorless | — |
| TBMA OH | Methanol | Pink | Active base |
| TBMA OH + DMA DMC | Methanol | Colorless | Dormant initiator |
| TBMA OH + DMA DMC | Ethanol | Colorless | Dormant initiator |
| TBMA OH + DMA DMC | 1-propanol | Colorless | Dormant initiator |
| TBMA OH + DMA DMC | 2-propanol | Colorless | Dormant initiator |
| Ion exchanged TBMA DMC | Ethanol | Colorless | Dormant initiator |
| Ion exchanged TBMA DMC | 1-propanol | Colorless | Dormant initiator |
| Ion exchanged TBMA DMC | 2-propanol | Colorless | Dormant initiator |

Comparative Example 4 (Versus Inventive Example 6)

About 1 ml of the catalysts prepared in example 4 using TBMA OH and DEtC with as-is concentration is each added to a 2 ml clear vial. Next, 2 drops of phenolphthalein indicator is added to the solution and mixed well. After mixing the final color change is observed as either pink or colorless and results are tabulated in table 8. A pink colored solution means the solution is basic and a colorless solutions means that the base is blocked from activity. Only the base in methanol is blocked by the carbonate but the base was not blocked by the carbonate in the other alcohols and remained active as base.

TABLE 8

| Materials | Solvent | Solution color | Comment |
|---|---|---|---|
| TBMA OH | Methanol | Pink | Active base |
| TBMA OH + DEtC | Methanol | Colorless | Blocked catalyst |
| TBMA OH + DEtC | Ethanol | Pink | Active base |
| TBMA OH + DEtC | 1-propanol | Pink | Active base |
| TBMA OH + DEtC | 2-propanol | Pink | Active base |

Inventive Example 7

The dormant carbamate initiator was employed in a crosslinkable coating composition as to formulate a nail polish system. The system utilized three coatings; a basecoat/primer, a color coat, and a topcoat to allow for comparison against commercial UV nail gel and conventional (solvent borne) nail polish systems, which also employ a three coat approach. Two nail polish systems (inventive example 7.1 and 7.2) were formulated based on the inventive crosslinkable composition.

Carbamate Initiator Synthesis:

Most of the methanol solvent from a 40 g tetrabutylammonium hydroxide (TBA OH) solution in methanol (1 M) was removed with a rotary evaporator in about 30 minutes at room temperature. Next, 40 grams of ethanol (EtOH) was added and most of the solvent was again removed in a similar manner. This procedure is repeated at least two more times until the methanol effectively has been replaced. The complete removal of methanol was confirmed by $^1$H NMR analysis. Next, 25 g of the TBAOH in EtOH (1.34 mmol base/g solution) solution was mixed with 6.4 g DMA DMC at room temperature and stirred for 1 hour using magnetic stirrer. The final light yellow solution had an initiator concentration of 1.38 mmol/g sample.

Base coat formulations: two different base coats were formulated.

Base coat A; formula ingredients: 4.55 wt. % of malonate resin (I) of example 6; 40.91 wt. % of malonate resin (II) of example 7; 19.91 wt. % of DTMPTA; 9.10 wt. % of butyl acetate (BA); 9.10% of ethyl acetate (EA); 1.83 wt. % of an alkyl ethoxylate wetting agent; and 14.60 wt. % of carbamate initiator. All the ingredients except the initiator were weighed into a 20 ml vial. The vial was capped and the mixture shaken until visually homogenous. The dormant carbamate initiator was then weighed into the mixture. The final mixture was capped and shaken for 30 seconds, and then applied using a 3 mil Bird type film applicator on a vitronail panel substrate.

Base coat B; formula ingredients: 7.28 wt. % of malonate resin (III) of example 8; 40.95 wt. % of malonate resin (II) of example 7; 19.93 wt. % of DTMPTA; 6.37 wt. % of BA; 9.10% of EA; 1.82 wt. % of an alkyl ethoxylate wetting agent; and 14.56 wt. % of carbamate initiator. All the ingredients except the initiator were weighed into a 20 ml vial. The vial was capped and the mixture shaken until visually homogenous. The dormant carbamate initiator was then weighed into the mixture. The final mixture was capped and shaken for 30 seconds, and then applied using a 3 mil Bird type film applicator on a vitronail panel substrate.

Color coat formulation: only one color coat A was formulated.

A Colorant Pigment Dispersion was prepared first. Formula ingredients: 62.65 wt. % of malonate resin (I) of example 6; 37.35 wt. % of Chemours TS-6200 white pigment. The resin was added to the stainless steel mixing vessel. Mixing of the resin was begun using a high speed dispersion mixer at 1.5 mm/s using a 50 mm mixing blade. The TS-6200 pigment was poured at a medium rate into the mixing resin. After all of the TS-6200 had been added, the mixing speed was increased to 7.85 m/s and held constant for 10 min. At the end of mixing, the mixture was poured into a storage jar and sealed.

Color coat A was formulated as follows: formula ingredients: 25.00 wt. % of the Colorant Pigment Dispersion; 9.15 wt. % of malonate resin (IV) of example 9; 6.10 wt. % malonate resin (II) of example 7; 35.37 wt. % of DTMPTA; 12.20 wt. % of BA; 2.43 wt. % of an alkyl ethoxylate wetting agent; and 9.75 wt. % of carbamate initiator. All the ingredients except the initiator were weighed into a 20 ml vial. The vial was capped and the mixture shaken until visually homogenous. The dormant carbamate initiator was then weighed into the mixture. The final mixture was capped and shaken for 30 seconds, and then applied over the dried base coat using a 3 mil Bird type film applicator.

Top coat formulations: two different top coats were formulated.

Top coat A; formula ingredients: 18.12 wt. % of malonate resin (I) of example 6; 10.87 wt. % of malonate resin (IV) of example 9; 7.25 wt. % of malonate resin (II) of example 7; 42.03 wt. % of DTMPTA; 7.25 wt. % of BA; 1.45 wt. % of 1,3-butanediol (BD); 1.44 wt. % of an alkyl ethoxylate wetting agent; and 11.59 wt. % of carbamate initiator. All the ingredients except the initiator were weighed into a 20 ml vial. The vial was capped and the mixture shaken until visually homogenous. The dormant carbamate initiator was then weighed into the mixture. The final mixture was capped and shaken for 30 seconds, and then applied over the dried color coat using a 3 mil Bird type film applicator.

Top coat B; formula ingredients: 28.82 wt. % of malonate resin (III) of example 8; 10.37 wt. % of malonate resin (IV) of example 9; 6.91 wt. % of malonate resin (II) of example 7; 40.08 wt. % of DTMPTA; 1.38 wt. % of BD; 1.38 wt. % of an alkyl ethoxylate wetting agent; and 11.06 wt. % of carbamate initiator. All the ingredients except the initiator were weighed into a 20 ml vial. The vial was capped and the mixture shaken until visually homogenous. The dormant carbamate initiator was then weighed into the mixture. The final mixture was capped and shaken for 30 seconds, and then applied over the dried color coat using a 3 mil Bird type film applicator.

Commercial systems: the commercial systems were applied in a similar manner also on vitronail substrate panels and cured as per instructions and procedures common to the industry.

The various coats of the nail coating systems are summarized in table 9.

TABLE 9

| Nail polish system | Base coat | Color coat | Top coat |
|---|---|---|---|
| Inventive 7.1 | Base coat A | Color coat A | Top coat A |
| Inventive 7.2 | Base coat B | Color coat A | Top coat B |
| UV nail gel | OPI GelColor Base coat | OPI GelColor Pink Flamenco Color coat | OPI GelColor Top coat |
| Conventional nail polish | Revlon ColorStay Gel-Smooth Base coat | Nina Ultra Pro Mariachi Color coat | Revlon Colorstay Gel Envy Diamond Top Coat |

Nail polish performance test results are shown in the table 10. Inventive coatings 7.1 and 7.2 exhibit comparable gloss and tack free dry times compared to the commercial references. The pencil hardness of these coatings are substantially greater than either of the references used in this testing. The acetone removal times of both inventive coatings were significantly faster than the commercial UV nail gel coating system. The conventional nail polish system was easiest to remove as expected, but the film was also extremely soft.

TABLE 10

| Nail polish system | Tack free time individual coat | | | Performance whole system | | |
|---|---|---|---|---|---|---|
| | Base coat (min) | Color coat (min) | Top coat (min) | 60° gloss | Pencil hardness | Acetone removal time (min) |
| Inventive 6.1 | 3 | 3.5 | 5.5 | 75 | 6.5 H | 13 |
| Inventive 6.2 | 2.3 | 3.8 | 5.3 | 72 | 8 H | 20 |
| UV nail gel | 4 | 3.5 | 3.5 | 73 | 3.5 H | 27 |
| Conventional nail polish | 1.25 | 2.5 | 1.3 | 81 | 9 B | 0.5 |

Inventive Example 8

The dormant carbamate initiator was used to cure a mixture of the acetoacetate modified polyol of example 10 and DTMPTA. A vial was charged with 46 wt. % acetoacetate modified polyol, 0.74 wt. % alkyl ethoxylate wetting agent, 36.86 wt. % DTMPTA and 9.2 wt. % BA. The vial was stirred until homogenous. Next, a carbamate initiator type II was prepared as in example 3 (46% in ethanol) and 7.4 wt. % of this initiator was then weighed into the coating mixture. The final mixture was capped and shaken for 30 seconds, and applied on a polycarbonate sheet using a 3 mil Bird type film applicator. The resulting coating cured quickly and was tack free in 20 minutes and had a glossy appearance (94 at 60°) and the gel time was 65 minutes.

As control, 45.87 wt. % of the STEPANPOL® PC-2011-225 polyol resin, 0.69 wt. % EFKA SL-3288; and 18.35 wt. % BA were weighed into a 20 ml vial and mixed. Next, 34.40% Basonat HB 100 isocyanate curative was added and the mixture stirred again before 0.69 wt. % Borchi-Kat 24 urethane catalyst was added and stirred in. A film was drawn down using a 3 mil Bird bar type film applicator. The resulting glossy coating (93 at 60°) cured tack free in 50 minutes but the gel time was only 2 minutes.

Inventive Example 9

Dormant carbamate initiator type II was prepared in example 3 from TBA OH in ethanol and varying amounts of this initiator system was used to assess cure speed using the malonate resin prepared under example 6 and TMPTA. The molar ratio for malonate methylene $CH_2$ to TMPTA was fixed at 3:2, while the ethanol content was kept as constant as possible at about 10 wt. % of the final formulation. The amount of initiator used is expressed as mole percent relative to the number of protons that can be abstracted to form activated Michael donor species. Films were applied on glass substrates to test tack free time and these are summarized in table 11. Some of the films with higher initiator concentrations gave a wrinkled appearance as the solvent content/package was not optimal in view of such fast cure speeds, however, increased carbamate initiator content provided faster cure rates.

TABLE 11

| | Carbamate initiator (mol %) | | | | | |
|---|---|---|---|---|---|---|
| | 0.83 | 1.67 | 3.33 | 6.67 | 10 | 13.33 |
| Tack free time (sec) | 600 | 455 | 328 | 213 | 154 | 100 |

Inventive Example 10

Carbamate initiator solutions where prepared as in example 4, but varying amounts of excess DMA DMC were employed in the synthesis procedure. A series of TBMA DMC initiator solutions with increasing amounts of excess DMA DMC was thus obtained and evaluated for efficacy as dormant carbamate initiator. In a general evaluation procedure, 2.0 g of malonate resin V of example 11 was mixed with 2.276 g of DTMPTA, 0.4 g of BA and about 0.67 g of the TBMA DMC initiator solution was added. The complete formulation was mixed well and then a 6 mil test film was applied on a polycarbonate substrate to test the curing behavior. Similar formulations were prepared to evaluate tack free time and gel time with results for the various TBMA DMC/DMADMC ratios shown in Table 12. Formulations with increasing amounts of excess DMA DMC show longer gel times, but the tack free time remains essentially the same.

TABLE 12

| TBMA DMCC (mmol) | DMA DMC (mmol) | Tack free time (min) | Gel time (hour) |
|---|---|---|---|
| 0.66 | 0.00 | 4 | 13 |
| 0.66 | 0.07 | 4 | 13 |
| 0.66 | 0.20 | 4 | 37 |
| 0.66 | 0.33 | 4 | 50 |
| 0.66 | 0.66 | 4 | 109 |

Similar coating formulations were employed to evaluate carbamate materials in various combinations. Isobutylammonium isobutylcarbamate (IBA IBC) was made by first dissolving 25 g of isobutylamine in 25 g of dichloromethane. $CO_2$ gas was passed through this solution and the reaction progress was followed for IBA IBC formation by NMR. The IBA IBC was obtained as a solid on dichloromethane and potentially amine was lost in the $CO_2$ flow with NMR confirming IBA IBC purity. Titrations were carried out to determine the acid/amine values and equivalent molecular wt. of the synthesized IBA IBC. Similar as in example 10, TBMA ethoxide in ethanol was prepared and mixed with IBA IBC to prepare a solution of tributylmethylammonium isobutylcarbamate (TBMA IBC). Tack free time and gel time results for the various carbamate combinations are shown in Table 13.

TABLE 13

| TBMA DMC mmol | DMA DMC mmol | IBA IBC mmol | TBMA IBC mmol | Tack free time (min) | Gel time (hour) |
|---|---|---|---|---|---|
| 0.44 | 0.22 | 0 | 0 | 5 | 37 |
| 0.43 | 0 | 0.21 | 0 | 14 | 87 |
| 0 | 0 | 0.28 | 0.45 | 30 | 105 |

Inventive Example 11

Unsubstituted and substituted malonate resins VI, VII and VIII of examples 12, 13 and 14 respectively, were each tested in a simple coating formulation of resin, DTMPTA crosslinker, BA solvent and a dormant initiator as prepared via example 4. All materials are mixed using a laboratory vortex mixer to create a homogeneous solution. Vials are prepared to observe gel time and 6 mil thick films are drawn on polycarbonate test panels to assess tack free time. Results are presented in Table 14. The substituted malonate resins show much longer gel times in comparison to the unsubstituted malonate resin while the cure speed determined in terms of tack free time remains very acceptable.

TABLE 14

| Resin type | Resin (g) | DTMPTA (g) | BA (g) | Initiator solution* (g) | Tack free time (min) | Gel time (days) |
|---|---|---|---|---|---|---|
| VI | 1 | 1.08 | 0.3 | 0.3 | 2 | overnight |
| VI | 1 | 0.54 | 0.3 | 0.3 | 3 | overnight |
| VII | 1 | 0.51 | 0.3 | 0.3 | 3 | 9 |
| VIII | 1 | 0.48 | 0.3 | 0.3 | 4 | 23 |

*Initiator solution contains 28.1 wt. % dormant initiator

Inventive Example 12

Model clear coat formulations were prepared with resin IX, X, XI or XII of examples 15, 16, 17 or 18 respectively, and DTMPTA and/or the DUDA crosslinker of example 19. A 1 to 1 molar ratio of active malonate methylene hydrogen to acrylate was maintained in the formulations and 10 wt. % of both BA solvent and dormant initiator solution as prepared via example 4 was added to the coating mixture. Vials were prepared to observe gel time and 3 mil thick films were drawn on aluminum test panels test panels to assess tack free time and mechanical properties. An OPI GelColor Top Coat commercial system was used as control reference and a 3 mil thick coating was applied and cured as per instructions and procedures common to the UV/LED nail gel industry. Results are presented in Table 15.

TABLE 15

| Resin system | DMPTA acrylate mol % | DUDA acrylate mol % | Tack free time (min) | Pencil Hardness | Conical mandrel | Reverse Impact | Direct Impact | Water Blush |
|---|---|---|---|---|---|---|---|---|
| OPI top coat | na* | na* | nm* | HB | 100% | 31% | 22% | Pass |
| IX | 0 | 100 | 7 | 9 H | 100% | 31% | 41% | Pass |
| IX | 30 | 70 | 3 | 8 H | 100% | 19% | 38% | Pass |
| X | 0 | 100 | 8 | 9 H | 100% | 63% | 34% | Pass |
| X | 100 | 0 | 4 | 8 H | 32% | 19% | 34% | Fail |
| XI | 100 | 0 | 4 | 8 H | 100% | 22% | 44% | Fail |
| XI | 0 | 100 | 5 | 4 H | 100% | 47% | 44% | Pass |
| XII | 90 | 10 | 4 | 6 H | 58% | 25% | 31% | Pass |
| XII | 50 | 50 | 3 | 9 H | 100% | 22% | 47% | Pass |
| XII | 0 | 100 | 4 | 9 H | 100% | 53% | 69% | Pass | na*: not applicable/nm*: not measured

Inventive Example 13

An inventive nail polish system was formulated as a two coat system (a Colorcoat and a Top Clearcoat), where the Colorcoat was applied directly on the bare nail surface, and then finished with the Top Clearcoat. Two pigment dispersions were prepared first, prior to formulating the color coat.

Preparation of an iron oxide blue pigment dispersion: 200 g of a resin as prepared under example 18 (resin XII) was weighed into a 500 ml jacketed mixing pot. The mixing pot was placed under a Dispermat high speed mixer equipped with 60 mm dual nylon disk pearl mill mixer attachment from BYK Instruments. The disk was lowered into the mixing pot to about 10 mm from the inside bottom of the pot. A water bath set to 140° F. was connected to the jacketed pot, and mixing was started at 500 rpm. Blue iron oxide powder (60 g; SunChroma Iron Blue supplied by Sun Chemical) was slowly poured into the pot while it was mixed. Then, 350 g of milling media were added to the pot. The milling media was 0.7-0.9 mm Yttria stabilized zirconium oxide beads supplied by Norstone Inc. The pot was covered, and the mixing speed was increased to 2500 rpm and maintained for 4 hrs. At the end of this time, the mixing was stopped. The contents of the mix pot were poured through a 190 micron Gerson paint filter screen (supplied by Gardco), in order to remove the beads. The final pigment dispersion was dark blue and was found to have a Hegman Fineness of Grind value of 7. The total net yield of this process was 57.5%.

Preparation of a titanium oxide white pigment dispersion: The same procedure as described for the iron oxide blue dispersion was used here using 200 g of a resin as prepared under example 18 (resin XII); 86 g titanium dioxide ($TiO_2$; supplied by Making Cosmetics); 350 g milling beads. Mixing/milling was performed at 140° F. at 2500 rpm for 4 hours, followed by filtering out the milling beads. A Hegman Grind of 7 was determined and the net yield of the white pigment dispersion from the procedure was 79%.

Colorcoat preparation: A blue Colorcoat was prepared as follows: into a 20 ml glass vial, 0.23 g of the above blue pigment dispersion and 0.54 g of the white pigment dispersion were added. An additional 0.56 g of a resin as prepared under example 18 (resin XII) was added to the vial. A stoichiometric excess of the crosslinker as prepared in example 19 was added, 3.5 g of DUDA, and solvent (0.68 g of n-butyl acetate) was added to the vial as well. The mixture was stirred by hand using a small metal spatula and the vial was capped. When time for the film application arrived, 0.48 g of dormant carbamate initiator as prepared under example 4 was added vial and the mixture was stirred using a spatula and then applied. Total mixing time was 1-2 min.

Top Clearcoat preparation: Into a 20 ml glass vial were weighed the following ingredients: 1.9 g of an unpigmented resin as prepared under example 18 (resin XII); 1.4 g of DUDA crosslinker as prepared under example 19, 1.7 g of DTMPTA crosslinker, 0.4 g BA, 0.06 g BD as anti-wrinkling additive, and 0.25 g of Polytex NX-55 gloss additive (supplied by Estron Chemical). The mixture was stirred by hand using a small metal spatula and the vial was capped. At the time of film application, 0.70 g of dormant carbamate initiator of Example 4 was added to the vial and the mixture was stirred using a spatula and then applied. Total mixing time was 1-2 min.

Inventive nail polish system (Colorcoat and Top Clearcoat) film application and testing: A 3 mil wet film of the Colorcoat was applied on aluminum and polycarbonate test panels. The films were allowed to air dry for 9-11 min prior to application of the Top Clearcoat over the dried Colorcoat film. The films were allowed to sit at ambient laboratory conditions overnight before evaluating their physical properties.

A commercial UV nail gel system (OPI GelColor) was used as comparison. The system consists of a base, color and top coat. The base coat was first applied and cured prior to application and curing of the OPI GelColor color coat, which was followed by application and curing of the OPI GelColor Top coat. The GelColor applications instructions were followed as closely as possible. All films were applied at a 3 mil wet film thickness and the system was allowed to equilibrate overnight before evaluation.

Performance results for the inventive and reference systems are shown in Table 16.

TABLE 16

| Nail polish system | Gloss 60° | Pencil Hardness | Conical mandrel | Reverse Impact | Direct Impact | Water Blush | Acetone removal (min) |
|---|---|---|---|---|---|---|---|
| Inventive | 85 | 3 H | 100% | 38% | 34% | Pass | 16 |
| OPI control | 83 | 3 H | 100% | 6% | 13% | Pass | >20 |

Inventive Example 14

FD&C and D&C dyes commonly used in nail polish and gel formulations were evaluated in Michael addition based crosslinkable compositions. Such colorants may also be used in other coating application industries such as automotive and industrial paints, architectural paints, plastics, adhesives and others. Concentrated dispersions of dye in malonate resin XIII from example 20 were prepared first. Said dispersions were then used to formulate simple color coat formulations. All color coats were formulated to generate specific comparative dye concentrations at 1% and 3% dye loading by weight. The amounts of raw materials added to the coating formulation are adjusted to achieve this desired dye loading. Finally, coatings of controlled thickness are prepared to evaluate certain applications and color properties. The following are specific examples how a dye dispersion and the color coat are prepared and serve as general preparative example:

Dye dispersion: First, 10.04 g of malonate resin XIII from example 20 was weighed directly into a tared 60 ml capacity mortar and 3.00 g of D&C Red 30 dye was weighed in next. A spatula was briefly used to hand blend the dye into the resin and a pestle was then used to grind the paste in the mortar to a fine consistency. The mixture was ground/milled by hand for approximately 10-25 minutes using the pestle and mortar until a Hegman Fineness of Grind value of 7 was achieved. The pigment dispersion was then transferred to a glass jar and sealed for later use.

Color coat: Into a 20 ml glass vial, 0.65 g of the above D&C Red 30 dye dispersion was added. An additional 1.95 g of the malonate resin XIII from example 20 was charged to the vial and 1.58 g of DTMPTA was added next. The materials in the vial were mixed by hand using a spatula to achieve homogeneity. After this, 0.41 g of BA was mixed in as well. The vial was sealed and vigorously shaken until homogenous. Test panels to be coated were placed into position at this point. Bird Bars (3 & 6 mil) for coating application were made ready. The glass vial was unsealed and 0.41 g of dormant carbamate initiator of example 4 is added. The lid was placed back on the vial. The complete mixture was vigorously shaken for 1-3 minutes to make it homogenous. Once mixing was completed, the mixture was promptly cast as films using the Bird Bars on 4"×6" polycarbonate panels. Tack free time was recorded and coating surface wrinkling was observed as the films cured. Decorative coatings applied on finger- and/or toe nails typically are about 1.0-1.5 mil thick, sometimes up to 2 mil thick per coating layer when applied by brush although even thicker coatings are applied by consumers that are less experienced.

Various dyes were thus evaluated and compared to a dye free (uncolored) control and results are shown in Table 17. The uncolored coating (used as a reference film) exhibits slight surface wrinkling, in the absence of dye. The amount of surface wrinkling is inherent in the resin/formula combination used for this evaluation. Any worsening of this surface wrinkling is considered less desirable.

TABLE 17

| D&C or FD&C dye name | Supplier | Dye Conc (by wt.) | Films-3 mils applied thickness | | Films-6 mils applied thickness | |
|---|---|---|---|---|---|---|
| | | | Tack free time (min) | Coating surface wrinkling | Tack free time (min) | Coating surface wrinkling |
| Blank Control | no dye used | no dye present | 1.7 | slight | 2.0 | slight |
| Annatto | Sensient Technolgy Corp. | 1% | 1.4 | none | 2.0 | none |
| Annatto | Sensient Technolgy Corp. | 3% | 2.0 | none | 2.7 | slight |
| Beta-Carotene | Sensient Technolgy Corp. | 1% | 1.5 | none | 2.0 | very slight |
| Beta-Carotene | Sensient Technolgy Corp. | 3% | 1.8 | none | 2.0 | very slight |
| Black 2 | MakingCosmetics Inc. | 1% | 1.5 | none | 2.2 | severe |
| Black 2 | MakingCosmetics Inc. | 3% | 4.4 | slight | 8.5 | severe |
| Blue 1 | Emerald Performance Materials | 1% | 1.6 | none | 2.3 | very slight |
| Blue 1 | Emerald Performance Materials | 3% | 2.3 | none | 3.3 | slight |
| Blue 2 | Spectra Colors Corp. | 1% | 1.1 | none | 2.1 | none |
| Blue 2 | Spectra Colors Corp. | 3% | 1.7 | slight | 3.0 | slight |
| Brown 1 | Sensient Technolgy Corp. | 1% | 1.8 | slight | 3.4 | slight |
| Brown 1 | Sensient Technolgy Corp. | 3% | 3.0 | slight | 3.8 | severe |
| Caramel | Sensient Technolgy Corp. | 1% | 1.5 | very slight | 2.0 | very slight |
| Caramel | Sensient Technolgy Corp. | 3% | 1.4 | very slight | 2.0 | very slight |
| Carmine Red | Emerald Performance Materials | 1% | 2.5 | none | 3.5 | very slight |
| Carmine Red | Emerald Performance Materials | 3% | 1.3 | very slight | 2.0 | very slight |
| Green 3 | Spectra Colors Corp. | 1% | 1.9 | none | 2.1 | slight |
| Green 3 | Spectra Colors Corp. | 3% | 2.1 | none | 2.9 | slight |
| Green 5 | Spectra Colors Corp. | 1% | 2.0 | none | 2.5 | none |
| Green 5 | Spectra Colors Corp. | 3% | 3.8 | none | 3.0 | slight |
| Green 6 | Spectra Colors Corp. | 1% | 1.7 | none | 2.2 | very slight |

TABLE 17-continued

| D&C or FD&C dye name | Supplier | Dye Conc (by wt.) | Films-3 mils applied thickness | | Films-6 mils applied thickness | |
|---|---|---|---|---|---|---|
| | | | Tack free time (min) | Coating surface wrinkling | Tack free time (min) | Coating surface wrinkling |
| Green 6 | Spectra Colors Corp. | 3% | 2.1 | slight | 2.7 | slight |
| Orange 4 | Spectra Colors Corp. | 1% | 3.7 | none | 4.3 | very slight |
| Orange 4 | Spectra Colors Corp. | 3% | 7.0 | slight | 9.2 | severe |
| Red 21 | Spectra Colors Corp. | 1% | 2.3 | none | 3.3 | slight |
| Red 21 | Spectra Colors Corp. | 3% | 3.2 | none | 4.3 | none |
| Red 22 | Emerald Performance Materials | 1% | 3.0 | none | 3.0 | slight |
| Red 22 | Emerald Performance Materials | 3% | 5.3 | none | 5.5 | severe |
| Red 27 | Spectra Colors Corp. | 1% | 2.3 | none | 3.5 | slight |
| Red 27 | Spectra Colors Corp. | 3% | 2.4 | slight | 4.3 | slight |
| Red 28 | Emerald Performance Materials | 1% | 2.8 | slight | 4.0 | slight |
| Red 28 | Emerald Performance Materials | 3% | 3.3 | slight | 5.3 | severe |
| Red 30 | Spectra Colors Corp. | 1% | 1.8 | slight | 2.2 | slight |
| Red 30 | Spectra Colors Corp. | 3% | 2.0 | none | 2.8 | slight |
| Red 33 | Emerald Performance Materials | 1% | 2.3 | none | 3.0 | slight |
| Red 33 | Emerald Performance Materials | 3% | 3.1 | slight | 4.2 | slight |
| Red 34 | Sentient Cosmetics Tech. | 1% | 1.8 | none | 3.3 | slight |
| Red 34 | Sentient Cosmetics Tech. | 3% | 2.3 | slight | 5.5 | severe |
| Red 36 | Spectra Colors Corp. | 1% | 2.3 | none | 3.9 | none |
| Red 36 | Spectra Colors Corp. | 3% | 3.0 | none | 4.5 | very slight |
| Red 4 | Spectra | 1% | 3.2 | very slight | 6.8 | severe |
| Red 4 | Spectra Colors Corp. | 3% | 18.0 | slight | 30.0 | severe |
| Red 40 | Spectra Colors Corp. | 1% | 2.2 | slight | 3.1 | slight |
| Red 40 | Spectra Colors Corp. | 3% | 3.8 | slight | 4.3 | slight |
| Red 6 | Spectra Colors Corp. | 1% | 2.0 | slight | 2.7 | none |
| Red 6 | Spectra Colors Corp. | 3% | 2.0 | slight | 2.6 | none |
| Red 7 | Spectra Colors Corp. | 1% | 2.0 | slight | 2.9 | slight |
| Red 7 | Spectra Colors Corp. | 3% | 2.5 | slight | 5.4 | severe |
| Violet 2 | Emerald Performance Materials | 1% | 1.6 | none | 2.2 | very slight |
| Violet 2 | Emerald Performance Materials | 3% | 2.5 | none | 3.2 | very slight |
| Yellow 10 | Spectra Colors Corp. | 1% | 2.5 | none | 4.3 | very slight |
| Yellow 10 | Spectra Colors Corp. | 3% | 3.3 | none | 9.0 | very slight |
| Yellow 11 | Spectra Colors Corp. | 1% | 2.0 | none | 2.2 | very slight |
| Yellow 11 | Spectra Colors Corp. | 3% | 2.5 | none | 3.5 | very slight |
| Yellow 5 | Spectra Colors Corp. | 1% | 2.0 | none | 2.9 | slight |
| Yellow 5 | Spectra Colors Corp. | 3% | 2.5 | slight | 3.4 | slight |
| Yellow 6 | Spectra Colors Corp. | 1% | 2.2 | none | 2.8 | very slight |
| Yellow 6 | Spectra Colors Corp. | 3% | 3.3 | slight | 4.0 | slight |

The films prepared at 3% dye concentration and 3 mil film wet applied film thickness, were additionally evaluated by color spectrophotometry to monitor color change upon aging. Once the applied coating became tack free, a timer was started. Color measurements were carried out for each film. Each coated panel was measured at 3 different points during the aging process: (1) 1 hr.; (2) overnight (>16 hrs); and (3) after 1 week. Color analyses were performed using a calibrated DataColor 800 Spectrophotometer to measure the coated panels. The panels sat in ambient laboratory conditions during the period of aging. The color measurement changes (delta values for a, b, l, and the total color change $\Delta E$, CIELAB system) for overnight and 1 week of aging were determined using the one hour color measurement as the reference point from which the instrument's software calculated the delta values. Whether a color change is noticeable to the eye is a matter of personal opinion for end users of nail color cosmetics. For purposes of this example, color changes of $\Delta E$ of $<=1.0$ were interpreted as Good. Color change of $\Delta E>1.0$ but $<=2.0$ were interpreted as Fair yet still considered acceptable as being viewed that such a color change would be likely detected by a trained eye only. Color changes of $\Delta E>2.0$ were less desirable as this color change is likely to be readily noticeable even to an untrained eye. A color change $\Delta E>4.0$ is significant, while a color change of $\Delta E>5$ is an entirely different color. Table 18 shows results for the color measurements.

TABLE 18

| Films-3 mils applied thickness dye name | Same day color analysis (reference point) | | | Overnight color change analysis | | | | One week color change analysis | | | |
|---|---|---|---|---|---|---|---|---|---|---|---|
| | L* Lightness 0 = Black 100 = White | a* +Red −Green | b* +Yellow −Blue | ΔL* | Δa* | Δb* | ΔE* total color difference | ΔL* | Δa* | Δb* | ΔE total color difference |
| Annatto | 51.65 | 25.71 | 49.80 | −0.59 | 1.43 | −0.91 | 1.80 | −0.54 | 0.86 | −1.62 | 1.91 |
| Beta-Carotene | 48.85 | 19.12 | 24.38 | −1.93 | 2.32 | −2.12 | 3.69 | 1.36 | −3.69 | −1.37 | 4.17 |
| Black 2 | 22.83 | −0.01 | −0.48 | 0.92 | −0.02 | 0.09 | 0.93 | 1.00 | −9.05 | −0.04 | 1.00 |
| Blue 1 | 29.59 | 13.41 | −7.86 | 4.18 | −8.57 | 11.39 | 14.86 | 13.23 | 1.56 | 23.72 | 27.21 |
| Blue 2 | 23.77 | 4.08 | −7.06 | 1.44 | 5.20 | −11.34 | 12.56 | 17.90 | −3.11 | −4.92 | 18.83 |
| Brown 1 | 36.11 | 37.55 | 21.69 | 1.03 | −0.29 | 0.96 | 1.43 | 2.42 | −2.54 | −0.18 | 3.51 |
| Caramel | 56.59 | 3.37 | 10.06 | −0.2 | 0.09 | 0.29 | 0.36 | −0.83 | 0.28 | 0.92 | 1.27 |
| Carmine Red | 37.16 | 25.48 | 1.61 | −0.6 | −1.01 | −0.02 | 1.18 | −2.46 | −1.94 | 0.26 | 3.14 |
| Green 3 | 23.79 | 4.86 | −8.46 | 1.26 | 3.84 | −9.04 | 9.90 | 22.05 | −5.3 | −0.3 | 22.69 |
| Green 5 | 24.68 | −5.2 | −0.67 | 0.70 | 0.37 | −0.82 | 1.14 | 1.11 | 1.01 | −0.33 | 1.53 |
| Green 6 | 26.01 | −2.17 | −2.64 | 0.26 | 0.55 | 0.38 | 0.71 | 2.10 | −1.46 | −0.86 | 2.70 |
| Orange 4 | 30.78 | 25.29 | 11.78 | −0.53 | −2.20 | −2.6 | 3.45 | 4.85 | 4.84 | 6.40 | 9.37 |
| Red 21 | 47.23 | 43.19 | 30.33 | 0.52 | −0.07 | 1.01 | 1.14 | 1.61 | −1.26 | 3.52 | 4.07 |
| Red 22 | 46.02 | 42.46 | 27.99 | 0.20 | −0.10 | 0.51 | 0.56 | 3.09 | −0.14 | 6.43 | 7.14 |
| Red 27 | 40.26 | 48.65 | 10.09 | 0.47 | −0.03 | 1.03 | 1.14 | −0.8 | 3.29 | 0.00 | 3.39 |
| Red 28 | 40.56 | 49.28 | 11.65 | 0.68 | 0.13 | 1.17 | 1.36 | 0.36 | 3.31 | 1.21 | 3.57 |
| Red 30 | 33.34 | 30.65 | 13.84 | −0.34 | −0.42 | 0.05 | 0.48 | 0.24 | −0.79 | −0.44 | 0.93 |
| Red 33 | 24.59 | 8.76 | 2.10 | 0.34 | 0.34 | 0.22 | 0.53 | 0.73 | 0.84 | 0.93 | 1.25 |
| Red 34 | 27.26 | 16.75 | 6.34 | −0.03 | 0.20 | −0.13 | 0.23 | 4.77 | 1.86 | 5.12 | 5.22 |
| Red 4 | 35.70 | 29.05 | 20.44 | −0.87 | −4.02 | −0.79 | 4.19 | −3.03 | 0.75 | −5.47 | 6.30 |
| Red 40 | 27.58 | 20.78 | 7.24 | 1.47 | −1.75 | −0.61 | 2.37 | 8.66 | 5.63 | 10.12 | 10.83 |
| Red 6 | 40.92 | 39.03 | 29.31 | −0.49 | −2.85 | −0.09 | 2.89 | −2.03 | −4.16 | −5.55 | 7.23 |
| Red 7 | 33.01 | 31.58 | 16.73 | 0.17 | 1.88 | 0.40 | 1.93 | 2.15 | 1.44 | 1.98 | 3.26 |
| Violet 2 | 25.09 | 5.12 | −1.48 | −1.13 | 0.35 | −0.83 | 1.44 | 3.58 | −0.22 | −4.47 | 5.73 |
| Yellow 10 | 56.22 | 7.70 | 51.62 | 0.86 | −0.88 | −3.35 | 3.57 | 0.15 | −0.32 | −3.76 | 3.77 |
| Yellow 11 | 61.10 | 1.84 | 57.23 | −0.06 | −1.53 | −1.7 | 2.29 | 0.43 | −3.38 | −3.7 | 5.03 |
| Yellow 5 | 54.80 | 14.19 | 53.08 | −0.13 | −0.07 | −0.25 | 0.29 | −0.43 | 0.03 | −1.64 | 1.70 |
| Yellow 6 | 33.05 | 17.16 | 5.73 | 1.22 | 3.34 | 1.94 | 4.05 | 3.19 | 5.37 | 3.01 | 7.37 |

Inventive Example 15

FD&C and D&C approved pigments commonly used in nail polish and gel formulations were evaluated in Michael addition based crosslinkable compositions. Such colorants may also be used in other industries such as automotive and industrial paints, architectural paints, plastics, adhesives and others. Concentrated dispersions of pigment in malonate resin XIII from example 20 were prepared first in a similar manner as described for the dye dispersion in the inventive example 14 above. Said dispersions were then used to formulate simple color coat formulations. All color coats were formulated to generate specific comparative pigment concentrations at 3% pigment loading by weight. The amounts of raw materials added to the coating formulation are adjusted to achieve this desired pigment loading. Finally, coatings of controlled thickness are prepared to evaluate certain applications and color properties. The following is an example how a pigment dispersion and color coat is prepared and serves as a general preparative example: A 40% concentrate dispersion of Chromium Oxide Green pigment in malonate resin XIII from example 20 was prepared by means of grinding the pigment in the resin with a mortar and pestle until the paste showed a Hegman Fineness of Grind value of 7. To prepare the coating formulation, 0.38 g of the 40% Chromium Oxide Green dispersion was combined with 2.23 g of malonate resin XIII from example 20, and 1.58 g of DTMPTA, mixed and then 0.41 g of BA was added to dilute prior to adding 0.41 g of dormant carbamate initiator of example 4. The complete mixture was vigorously shaken to make it homogenous. Once mixing was completed, the coating mixture was promptly applied as a film to polycarbonate substrate panels. Films were cast at 3 and 6 mil wet thickness and evaluated for tack free time, surface wrinkling and overnight color fading. Coating surface wrinkling and overnight color fading are visual observations about the surface roughness and change of initial color after sitting overnight. The gel time and brushability time were also determined for the mixture. Acceptable tack free times with reasonable brushability and gel times are achieved, while color fading was also deemed acceptable. Results are summarized in Table 19.

TABLE 19

| Pigment description | Supplier | Brushability time (hours) | Gel time (hours) | Films-3 mils applied thickness | | | Films-6 mils applied thickness | | |
|---|---|---|---|---|---|---|---|---|---|
| | | | | Tack free time (min) | Coating surface wrinkling | Overnight color fading | Tack free time (min) | Coating surface wrinkling | Overnight color fading |
| Blank control (unpigmented) | n/a | 3.3 | >6 | 1.5 | none | n/a | 2.2 | slight | n/a |
| 3% Aluminum Powder | Altana AG | <0.5 | 0.5 | 2.0 | none | none | 3.0 | none | none |

TABLE 19-continued

| | | | | Films-3 mils applied thickness | | | Films-6 mils applied thickness | | |
|---|---|---|---|---|---|---|---|---|---|
| Pigment description | Supplier | Brushability time (hours) | Gel time (hours) | Tack free time (min) | Coating surface wrinkling | Overnight color fading | Tack free time (min) | Coating surface wrinkling | Overnight color fading |
| 3% Bismuth Oxychloride | BASF SE | >1.0 | >1 | 1.7 | slight | none | 2.5 | slight | none |
| 3% Black Iron Oxide | MakingCosmetics Inc. | >1.0 | >1 | 1.5 | none | none | 1.8 | none | none |
| 3% Brown Iron oxide | MakingCosmetics Inc. | 5.0 | >8 | 1.7 | slight | none | 2.8 | moderate | none |
| 3% Chromium Oxide Green | MakingCosmetics Inc. | 5.0 | >8 | 1.7 | slight | none | 2.1 | moderate | none |
| 3% Iron Blue (Ferric Ferrocyanide Blue) | Sun Chemical Corp. | 5.0 | >8 | 1.5 | slight | none | 2.1 | moderate | none |
| 3% Manganese Violet | Sun Chemical Corp. | >1.0 | >1 | 1.3 | none | none | 2.0 | slight | none |
| 3% Mica | MakingCosmetics Inc. | 1.0 | >1 | 1.4 | none | none | 2.0 | none | none |
| 3% Red Iron Oxide | MakingCosmetics Inc. | 2.3 | >5 | 1.8 | none | none | 2.8 | slight | none |
| 3% Titanium Dioxide | Sun Chemical Corp. | 5.0 | >8 | 1.8 | none | none | 2.5 | moderate | none |
| 3% Ultramarine Blue | Ferro Corp. | >1.0 | >1 | 1.8 | none | slight | 2.7 | slight | slight |
| 3% Ultramarine Pink | Ferro Corp. | >1.0 | >1 | 2.0 | none | slight | 2.5 | none | slight |
| 3% Ultramarine Violet | Ferro Corp. | >1.0 | >1 | 1.8 | none | none | 2.5 | slight | none |
| 3% Yellow Iron Oxide | Sun Chemical Corp. | 2.0 | >3 | 2.0 | severe | none | 4.7 | severe | none |

List of Chemical Acronyms Used in the Examples

BA butyl acetate
BD 1,3-butanediol
EA ethyl acetate
DEG diethylene glycol
DEGMEE diethylene glycol monoethylether
DEEM diethyl ethylmalonate
DEM diethyl malonate
DEMM diethyl methylmalonate
DEtC diethyl carbonate
DMA DMC dimethylammonium dimethylcarbamate
DMeC dimethylcarbonate
DTMPTA di-trimethylolpropane tetraacrylate
DUDA diurethane diacrylate
EtOH ethanol
Gly glycerol
HCl hydrochloric acid
HD 1,6-hexanediol
HEA 2-hydroxyethyl acrylate
IBA IBC isobutylammonium isobutylcarbamate
PD 1,3-propanediol
PEG 300 polyethylene glycol, Mw=300
tBAA tert-butyl acetoacetate
TBA DMC tetrabutylammonium dimethylcarbamate
TBA OH tetrabutylammonium hydroxide
TBMA tributylmethylammonium
TBMA Cl tributylmethylammonium chloride
TBMA DMC tributylmethylammonium dimethylcarbamate
TBMA IBC tributylmethylammonium isobutylcarbamate
THF tetrahydrofuran
TMDI trimethylhexamethylene diisocyanate
TMP trimethylolpropane
TMPTA trimethylolpropane triacrylate The present disclosure may be embodied in other specific forms without departing from the spirit or essential attributes of the invention. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

The invention claimed is:

1. A crosslinkable coating composition comprising:
    ingredient A that has at least two protons that can be activated to form a Michael carbanion donor;
    ingredient B that functions as a Michael acceptor having at least two ethylenically unsaturated functionalities each activated by an electron-withdrawing group;
    an additive selected from the group consisting of wetting agents, defoamers, rheological control agents, ultraviolet (UV) light stabilizers, dispersing agents, flow and leveling agents, optical brighteners, gloss additives, radical inhibitors, radical initiators, adhesion promotors, plasticizers and combinations thereof;

and a dormant carbamate initiator of Formula (1)

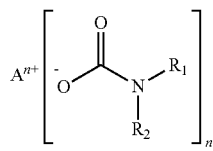

wherein $R_1$ and $R_2$ can be independently selected from hydrogen, a linear or branched substituted or unsubstituted alkyl group having 1 to 22 carbon atoms; 1 to 8 carbon atoms; or 1 to 4 carbon atoms; and $A^{n+}$ is a cationic species or polymer and n is an integer equal or greater than 1 with the proviso that $A^{n+}$ is not an acidic hydrogen; and optionally further comprising ammonium carbamate ($H_2NR_1R_2^{+-}OC=ONR_1R_2$).

2. The crosslinkable coating composition according to claim 1, wherein the ingredient A is independently selected from a malonate group containing compound, a malonate group containing oligomer, a malonate group containing polymer, an acetoacetate group containing compound, an acetoacetate group containing oligomer, an acetoacetate group containing polymer or combinations thereof.

3. The crosslinkable coating composition according to claim 2, wherein the malonate group containing compound, malonate group containing oligomer, malonate group containing polymer, an acetoacetate group containing compound, acetoacetate group containing oligomer, or acetoacetate group containing polymer are each selected from the group consisting of: polyurethanes, polyesters, polyacrylates, epoxy polymers, polyamides, polyesteramides or polyvinyl polymers, wherein such compounds, oligomers or polymers have (i) a malonate group, (ii) an acetoacetate group or (iii) combinations thereof located in a main chain of such compound or oligomer or polymer or a side chain of such compound or oligomer or polymer.

4. The crosslinkable coating composition according to claim 3, wherein ingredient B is selected from the group consisting of acrylates, fumarates, maleates and combinations thereof.

5. The crosslinkable coating composition according to claim 4, wherein the acrylate is independently selected from the group consisting of hexanediol diacrylate, trimethylolpropane triacrylate, pentaerythritol triacrylate, di-trimethylolpropane tetraacrylate, bis(2-hydroxyethyl acrylate) trimethylhexyl dicarbamate, bis(2-hydroxyethyl acrylate), 1,3,3-trimethylcyclohexyl dicarbamate, bis(2-hydroxyethyl acrylate) methylene dicyclohexyl dicarbamate and combinations thereof.

6. The crosslinkable coating composition according to claim 3, wherein ingredient B is independently selected from the group consisting of polyesters, polyurethanes, polyethers and/or alkyd resins each containing at least two pendant ethylenically unsaturated groups each activated by an electron-withdrawing group.

7. The crosslinkable coating composition according to claim 3, wherein ingredient B is independently selected from the group consisting of polyesters, polyurethanes, polyethers and/or alkyd resins each containing at least one pendant acryloyl functional group.

8. The crosslinkable coating composition according to claim 3, further comprising an ingredient D having one or more reactive protons that are more acidic than the protons of ingredient A, with respect to pKa.

9. The crosslinkable coating composition according to claim 3, further comprising less than 10 wt. %; 5 wt. %; 1 wt. %; 0.1 wt. %; 0.01 wt. % water.

10. The crosslinkable coating composition according to claim 3, being substantially free of water.

11. The crosslinkable coating composition according to claim 1, further comprising an organic solvent.

12. The crosslinkable coating composition according to claim 11, wherein the organic solvent is independently selected from the group consisting of an alcohol, ester, ether, glycol ether, ketone, aromatic and combinations thereof.

13. The crosslinkable coating composition according to claim 12, wherein the alcohol is independently selected from the group consisting of methanol, ethanol, iso-propanol, butanol, iso-butanol, t-butanol and combinations thereof.

14. The crosslinkable coating composition according to claim 1, further comprising a second dormant carbamate initiator of Formula (1)

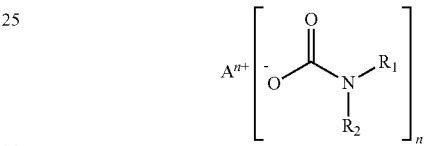

wherein $R_1$ and $R_2$ can be independently selected from hydrogen, a linear or branched substituted or unsubstituted alkyl group having 1 to 22 carbon atoms; 1 to 8 carbon atoms; or 1 to 4 carbon atoms; and $A^{n+}$ is a cationic species or polymer and n is an integer equal or greater than 1 with the proviso that $A^{n+}$ is not an acidic hydrogen.

15. The crosslinkable coating composition according to claim 14, wherein $A^{+n}$ is a monovalent quaternary ammonium compound of Formula (2)

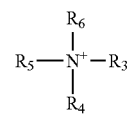

wherein $R_3$, $R_4$ and $R_5$ are independently selected from linear or branched alkyl chains having from 1 to 22 carbon atoms; or 1 to 8 carbon atoms and combinations thereof; and wherein $R_6$ is independently selected from the group consisting of: methyl, an alkyl group having from 2 to 6 carbon atoms or a benzyl group.

16. The crosslinkable coating composition according to claim 1, wherein the dormant carbamate initiator initiates Michael Addition to achieve cross linking when the crosslinkable coating composition is applied to a surface.

17. A coating composition comprising the crosslinkable coating composition according to claim 1.

* * * * *